(12) United States Patent
Foreman et al.

(10) Patent No.: US 11,598,719 B2
(45) Date of Patent: Mar. 7, 2023

(54) METHOD, COMPUTER PROGRAMME AND SYSTEM FOR ANALYSING A SAMPLE COMPRISING IDENTIFYING OR SORTING CELLS ACCORDING TO THE FTIR SPECTRUM EACH CELL PRODUCES

(71) Applicant: Sierra Medical Ltd, Barleythorpe (GB)

(72) Inventors: Liberty Foreman, Witney (GB);
Katherine Willets, Steventon (GB)

(73) Assignee: Sierra Medical Ltd, Barleythorpe (GB)

( * ) Notice: Subject to any disclaimer, the term of this patent is extended or adjusted under 35 U.S.C. 154(b) by 0 days.

(21) Appl. No.: 17/023,400

(22) Filed: Sep. 17, 2020

(65) Prior Publication Data

US 2021/0239607 A1    Aug. 5, 2021

Related U.S. Application Data

(63) Continuation of application No. 15/758,906, filed as application No. PCT/GB2016/052794 on Sep. 9, 2016, now Pat. No. 10,809,190.

(30) Foreign Application Priority Data

Sep. 10, 2015  (GB) .................................... 1516056

(51) Int. Cl.
| | | |
|---|---|---|
| *G01N 21/35* | (2014.01) | |
| *G01N 21/359* | (2014.01) | |
| *G01N 21/552* | (2014.01) | |
| *G01N 21/27* | (2006.01) | |
| *G01N 33/574* | (2006.01) | |
| *G01N 21/3563* | (2014.01) | |

(52) U.S. Cl.
CPC ......... *G01N 21/359* (2013.01); *G01N 21/274* (2013.01); *G01N 21/3563* (2013.01); *G01N 21/552* (2013.01); *G01N 33/57407* (2013.01); *G01N 2021/3595* (2013.01); *G01N 2201/1293* (2013.01)

(58) Field of Classification Search
CPC ............... G01N 21/359; G01N 21/274; G01N 21/3563; G01N 21/552; G01N 33/57407
See application file for complete search history.

(56) References Cited

U.S. PATENT DOCUMENTS 5,945,674 A * 8/1999 Dukor .................. G01N 21/552
250/341.8
6,887,711 B1 * 5/2005 Diem ................. G01N 15/1456
436/164

(Continued)

OTHER PUBLICATIONS

Patents Act 1977: Examination Report under Section 18(3) dated Apr. 23, 2021 From the Intellectual Property Office of the United Kingdom of Great Britain Re. Application No. 1516056.7 (3 Pages).

(Continued)

*Primary Examiner* — Hugh Maupin

(57) ABSTRACT

The invention relates to a method for improving the screening of histological samples, especially samples that may include cancerous or precancerous cells, or cells having other disease states. The method involves analysing a sample obtained from a subject and comprises the steps of providing the spectra produced by scanning the sample using FTIR spectroscopy and identifying or sorting the cells in the sample according to the spectrum each produces.

19 Claims, 21 Drawing Sheets

(56) References Cited

U.S. PATENT DOCUMENTS

| | | | |
|---|---|---|---|
| 2006/0155178 A1* | 7/2006 | Backman ............... | G01N 33/48 600/315 |
| 2012/0082362 A1* | 4/2012 | Diem ..................... | G01N 21/31 382/133 |
| 2018/0025210 A1* | 1/2018 | Remiszewski ......... | G06V 20/69 382/133 |

OTHER PUBLICATIONS

Foreman et al. "OC-015 High Grade Dysplasia Arising In Barrett's Oesophagus Can Be Accurately Diagnosed Combining Fourier Transform Infrared Spectroscopy And Single Element Attenuated Total Reflectance Ftir Data", BMJ Journals, Gut,63(Suppl 1): 2P.,Abstract. Jun. 2014.

* cited by examiner

Figure 3A  Figure 3B  Figure 3C
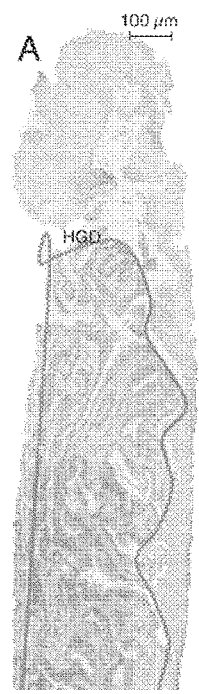
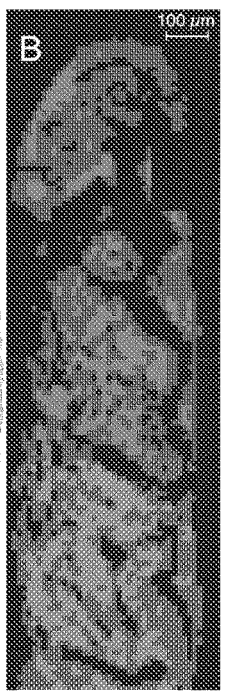
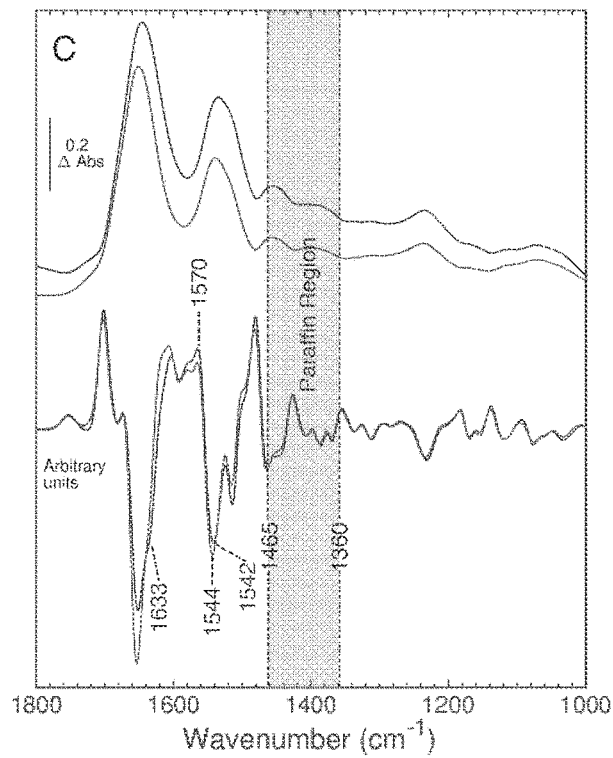
Figure 4A
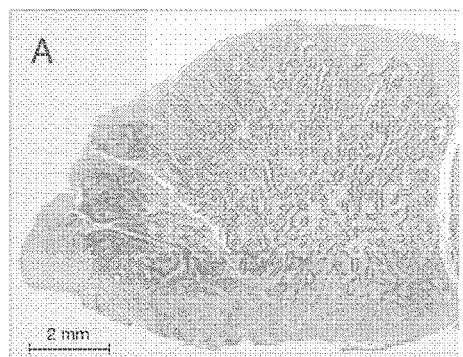
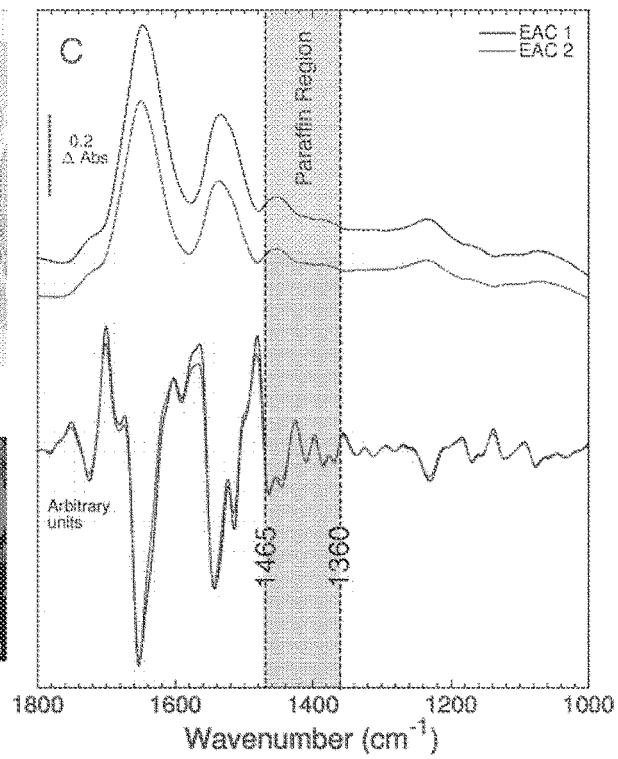
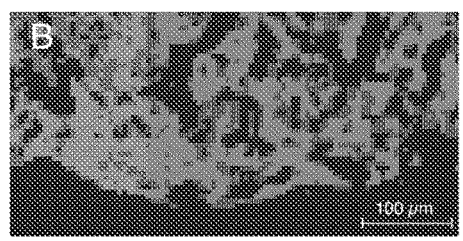
Figure 4B
Figure 4C Figure 5A
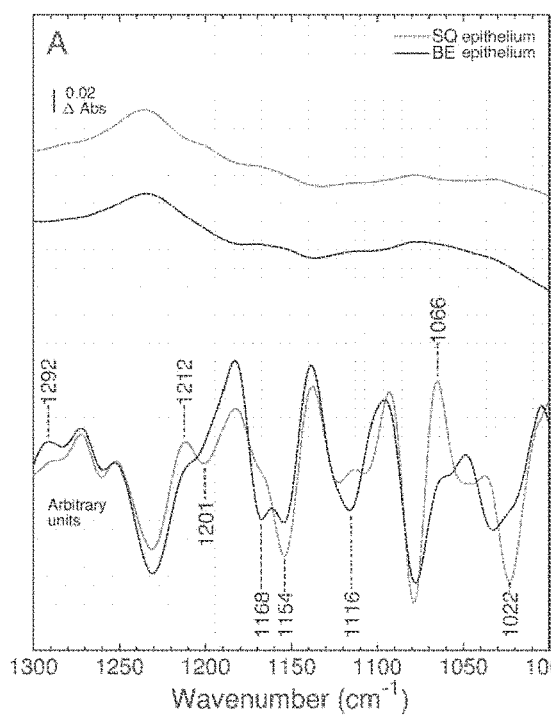
Figure 5B
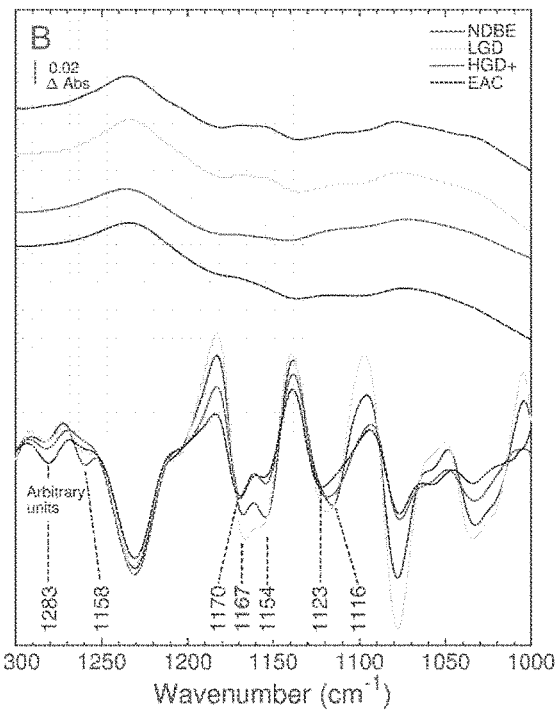
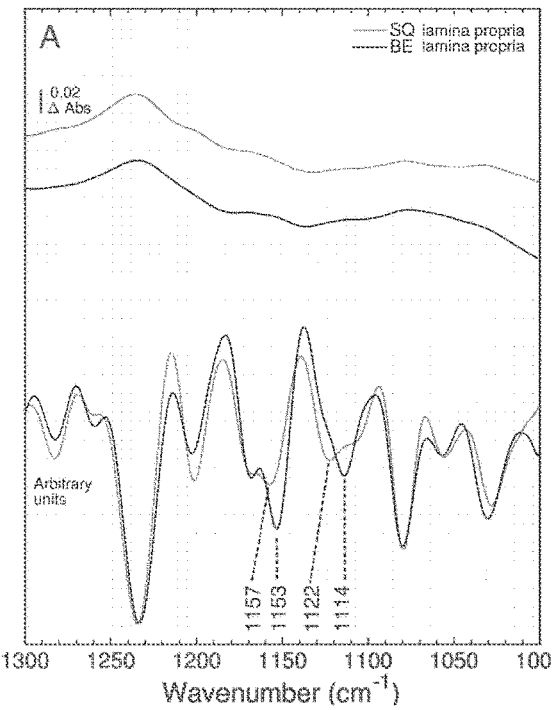
Figure 6A
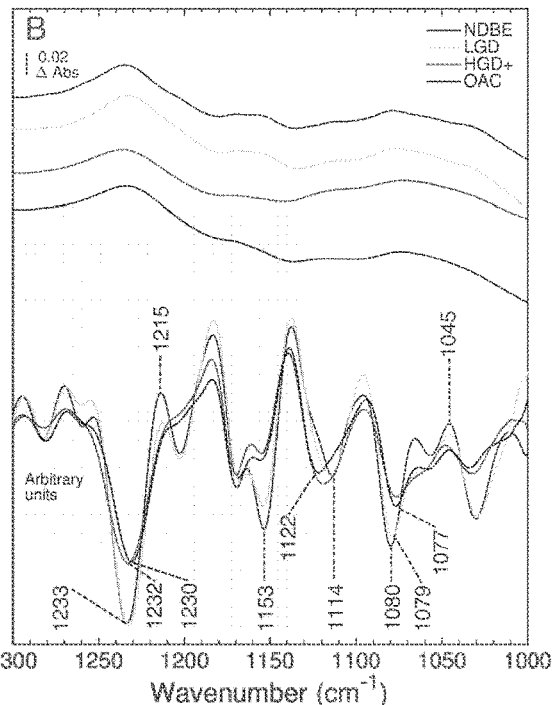
Figure 6B

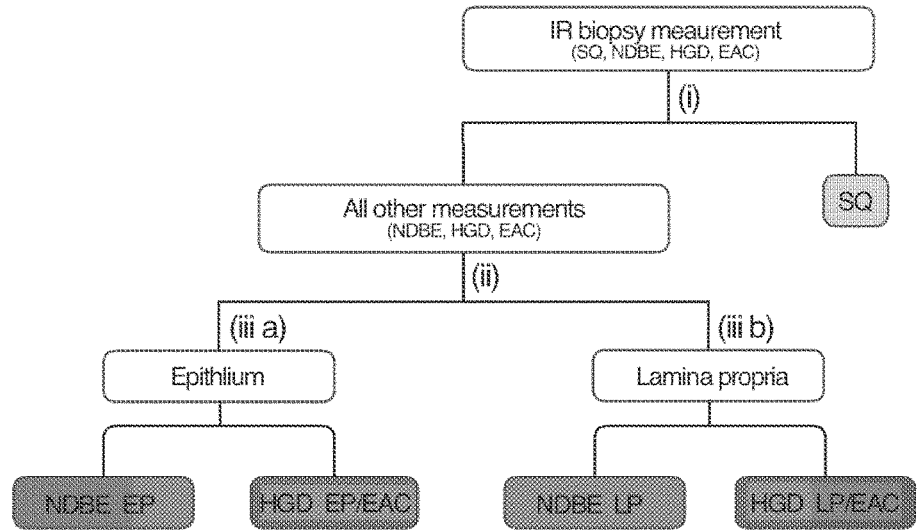
Figure 7.
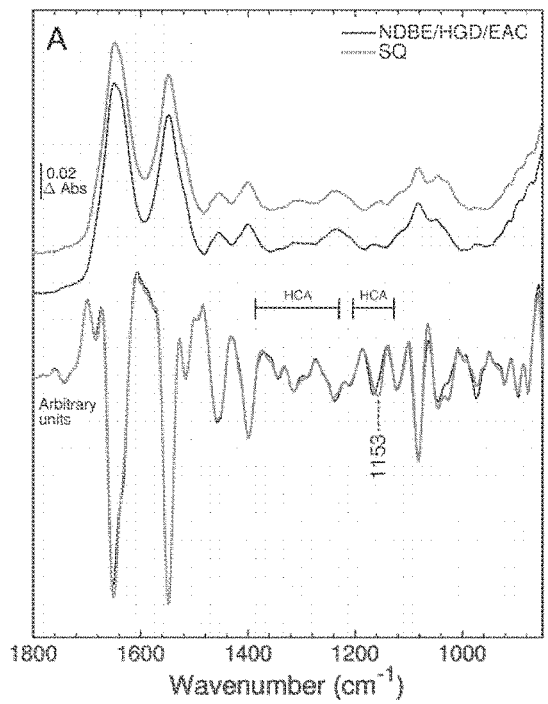 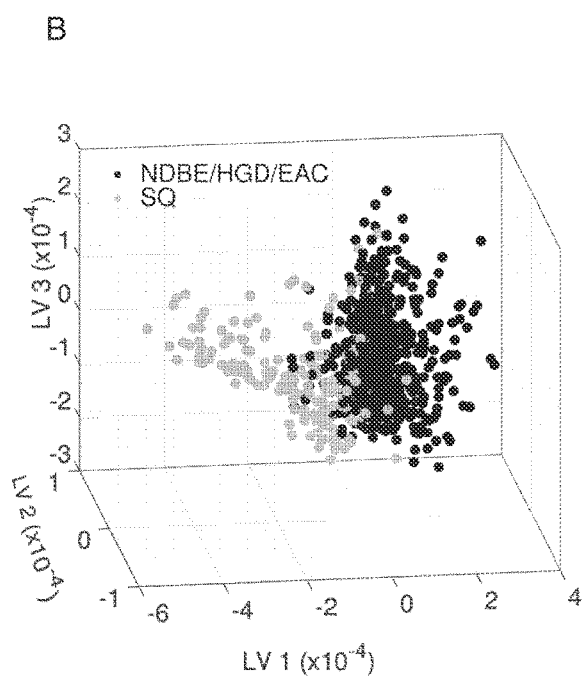
Figure 8A
Figure 8B

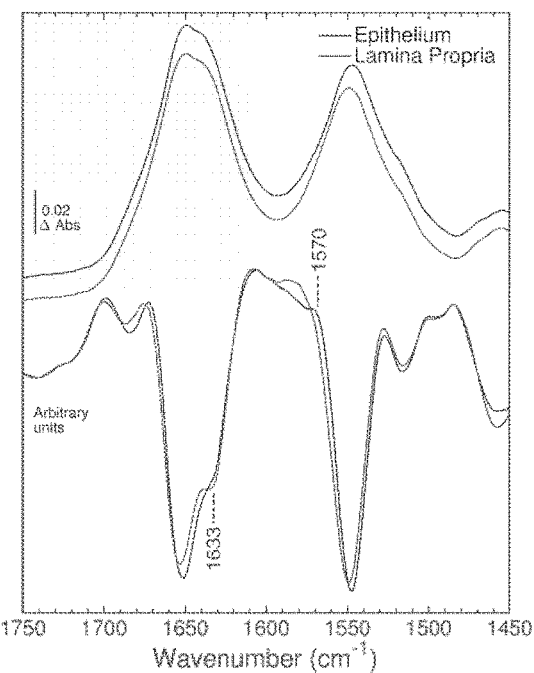
Figure 9
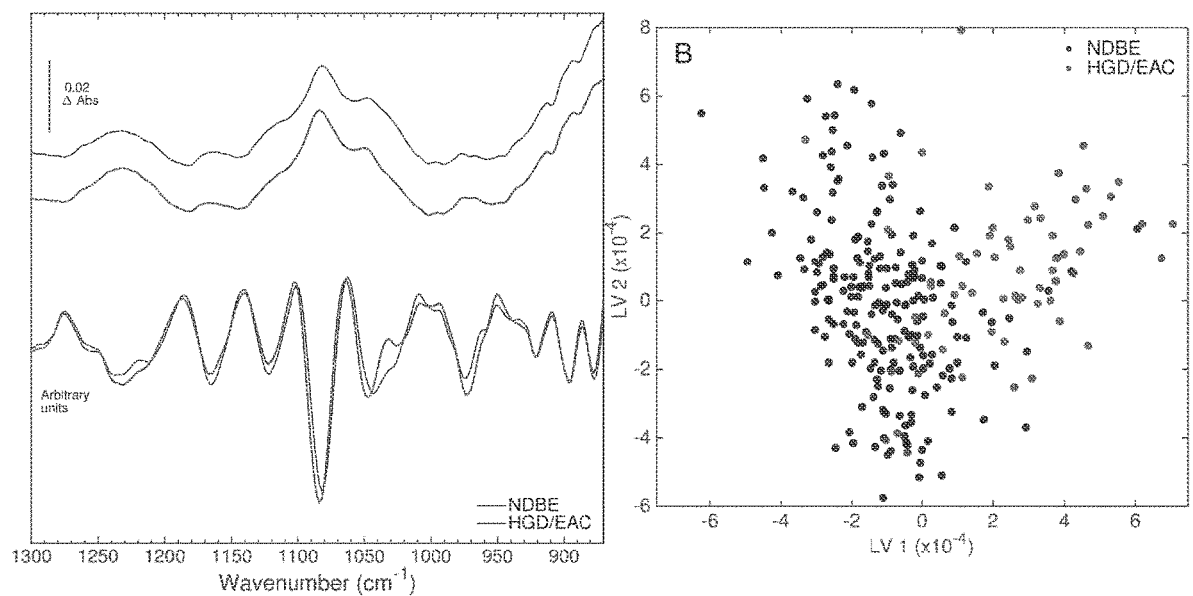
Figure 10A
Figure 10B

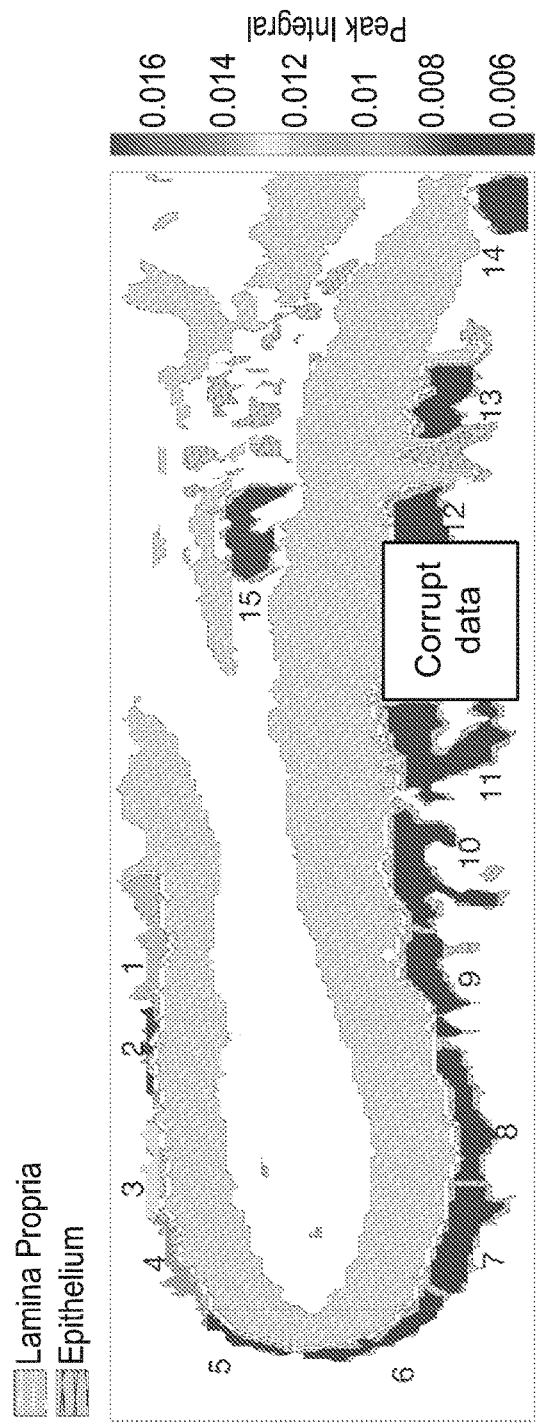 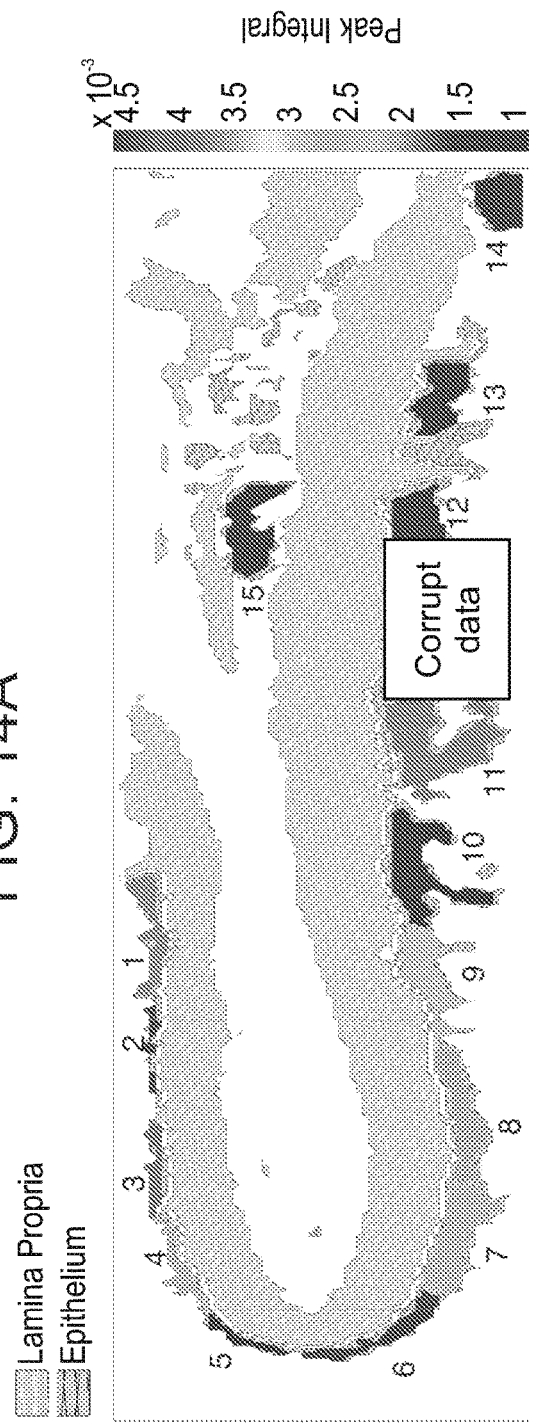
FIG. 14A
FIG. 14B

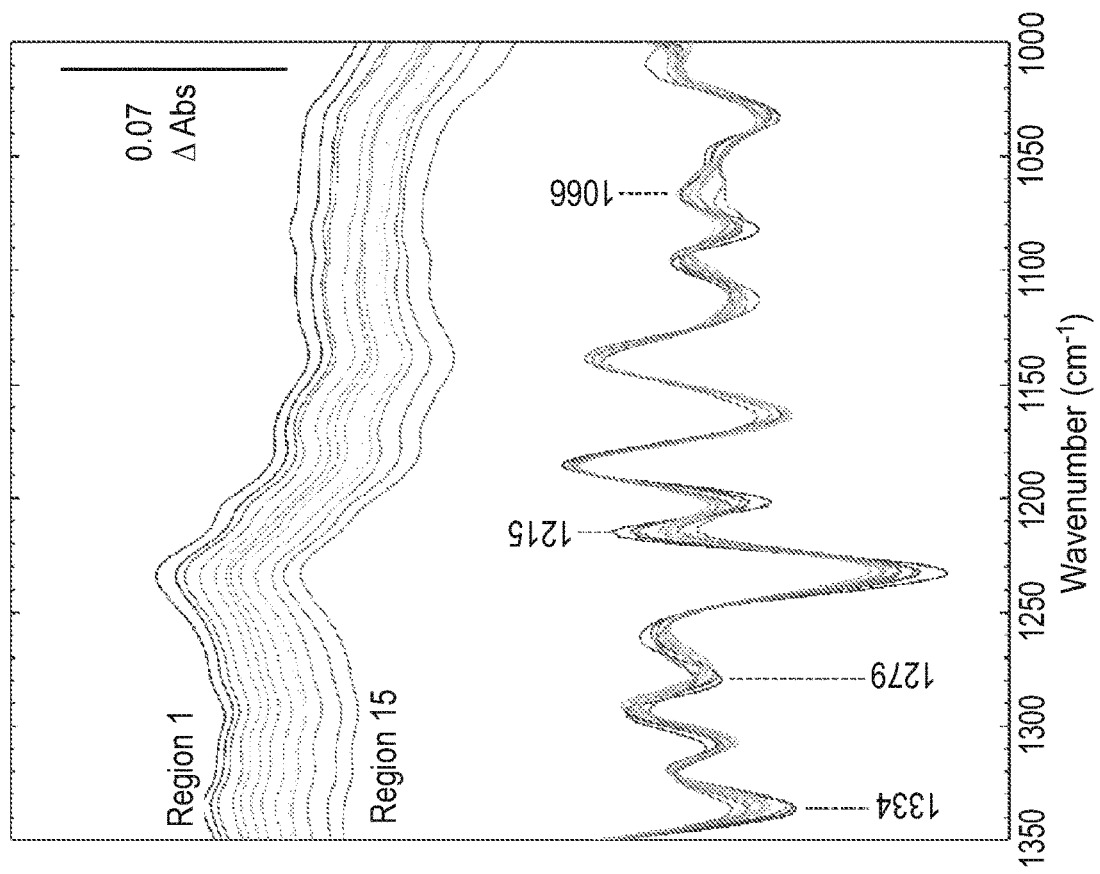
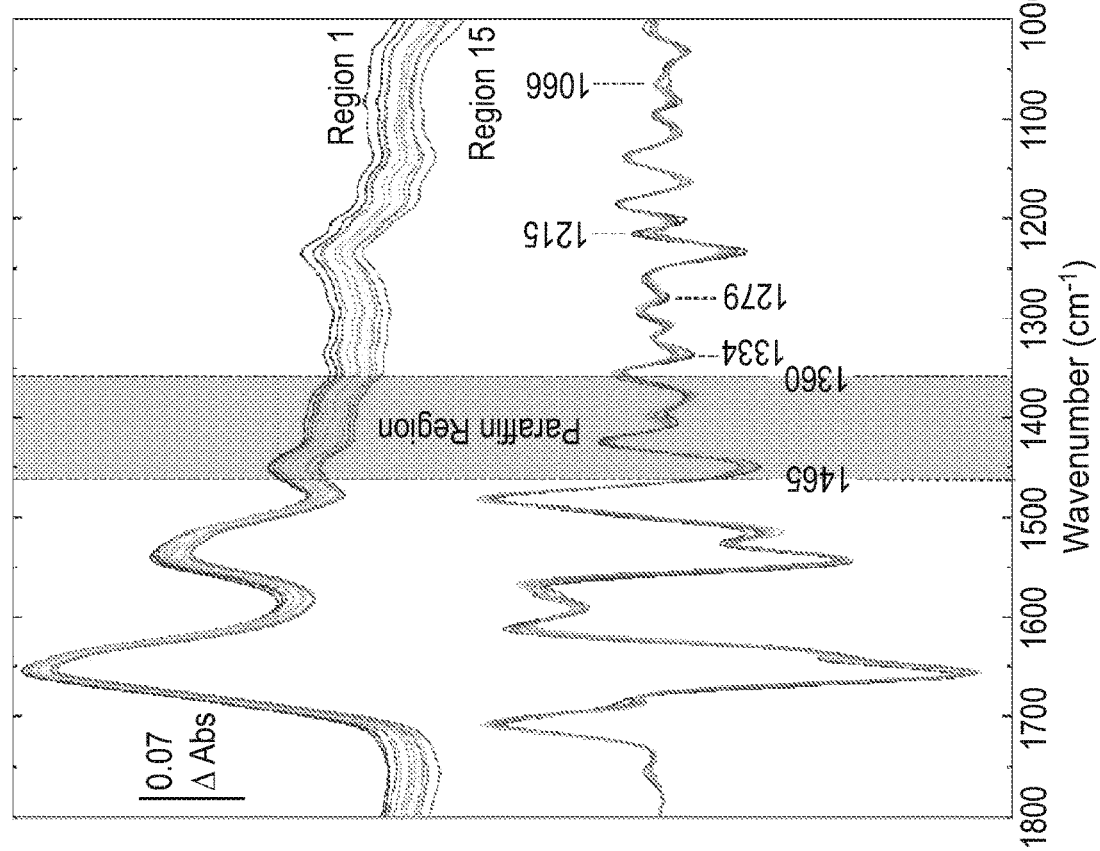
FIG. 17B
FIG. 17A

METHOD, COMPUTER PROGRAMME AND SYSTEM FOR ANALYSING A SAMPLE COMPRISING IDENTIFYING OR SORTING CELLS ACCORDING TO THE FTIR SPECTRUM EACH CELL PRODUCES

RELATED APPLICATIONS

This application is a Continuation of U.S. patent application Ser. No. 15/758,906 filed on Mar. 9, 2018, which is a National Phase of PCT Patent Application No. PCT/GB2016/052794 having International filing date of Sep. 9, 2016, which, which claims the benefit of priority of United Kingdom Patent Application No. 1516056.7 filed on Sep. 10, 2015. The contents of the above applications are all incorporated by reference as if fully set forth herein in their entirety.

FIELD OF THE INVENTION

The invention relates to a method for improving the screening of histological samples, especially samples that may include cancerous or precancerous cells, or cells having other disease states.

BACKGROUND TO THE INVENTION

There is a continuing need for an improvement to the methods available for screening for and monitoring cancer and tissue likely to develop into cancer. Early diagnosis significantly improves the likelihood of survival. Using a particular cancer, esophageal adenocarcinoma (EAC) as a starting point, the inventors have developed techniques for the improved identification and diagnosis of cancerous and precancerous tissue, the techniques being applicable to a variety of cancers, especially carcinomas.

The prognosis for EAC is poor with a 5 year survival rate of only 17%[1] and an incidence that has grown at approximately 2% per annum from 1999-2008 in the western population[2]. Barrett's esophagus (BE) is the recognized precursory lesion to EAC and occurs in patients with chronic gastroesophageal reflux disorder (GERD). Transformation to EAC occurs through a series of physiological stages. First there is columnar metaplasia of the native squamous (SQ) epithelium, which is referred to as non-dysplastic BE (NDBE), through low-grade dysplasia (LGD), high-grade dysplasia (HGD) and then EAC. The risk of progression from metaplastic columnar epithelium/NDBE to EAC is between 0.3-0.5%[3,4]. Once HGD develops, however, the risk of progression to EAC can be as high as 40-60% within 5 years if left untreated[4]. The treatment of patients at the LGD/early HGD stages has changed dramatically over the past 5 years. With these advances, the British Society of Gastroenterology (BSG) recommends that patients diagnosed with BE should undergo endoscopic surveillance every 2-5 years[5]. New, minimally invasive endoscopic therapies such as radiofrequency ablation (RFA)[6] and endoscopic mucosal resection (EMR) can provide curative therapy in 80-90% of LGD/HGD patients[7].

BE surveillance follows the Seattle protocol[8], involving sampling with quadratic biopsies every 1-2 cm along the visible columnar epithelium of the esophagus. These biopsies are subsequently sent for qualitative histopathological analysis. However, this process is time-consuming and expensive and there remains a significant degree of variability for diagnosing dysplasia even among expert pathologists[9,10]. Various methods to increase accuracy and ease of diagnosis have been investigated. For example, attempts have been made to identify biomarkers in biopsy analyses[11]. Advances in wide-field endoscopic imaging methods in vivo include using visible light[12-14] or optical coherence tomography[15]. Alternative solutions have been offered by point measurement techniques using elastic scattering spectroscopy[16,17] or confocal microscopy[18,19]. However, in all cases, high equipment and/or operational costs, together with insufficient consistency of outcomes, have precluded their adoption for routine clinical use[20,21]. Hence, a viable additional diagnostic/screening method of sufficient accuracy that can be implemented in the clinic remains a high priority.

FTIR and Raman vibrational spectroscopies are increasingly being investigated as possible diagnostic tools for a range of diseases as they can provide information on cellular changes in DNA, protein, carbohydrates and other metabolites[22,23]. Both FTIR[24-27,28], and Raman[29,30-34] spectroscopy have also been applied to BE diagnosis. FTIR studies have included microspectroscopic analyses of tissue[25], or of stem cells derived from BE and EAC cell lines[26], and macro-ATR-FTIR imaging[35] to distinguish SQ from BE[24] or EAC[27,28]. Multivariate analyses of Raman images of excised BE tissue sections at various stages of disease progression[29-32] led to identification of individual cell types[33] and their specific biochemical changes[30]. More recently, spectra of ex-vivo tissue samples have been obtained with Raman probes, aimed at future possible in vivo use[34,36,37].

The inventors have developed techniques using single element ATR-FTIR spectroscopy resulting in a relatively simple way to provide a clinically feasible method for rapid, point-of-care screening of dysplastic BE biopsies before histological analysis. The method may be used to aid clinicians' decision making, leading to a reduced need for detailed histological review of samples, which will ultimately lower the cost of BE surveillance and may enable immediate treatment for those identified with dysplastic BE. These methods can also be applied to biopsies of other potentially cancerous and precancerous tissues, particularly those of epithelial tissues. Specifically, the inventors have found that it is possible to separate the averaged surface of a biopsy into the predominant tissue type present by using the spectral characteristics of different tissue types found using FTIR imaging.

Having identified that the analysis method could be applied to cancerous and precancerous tissue, the inventors then applied it to other cell types and identified that it could be used to sort a variety of cell types easily and accurately.

SUMMARY OF THE INVENTION

According to a first aspect of the invention, there is provided a method for analysing a sample obtained from a subject, comprising the steps of:
  a) Providing the spectra produced by scanning the sample using FTIR spectroscopy; and
  b) separating the cells in the sample according to the spectrum each produces.

The inventors have found that it is possible to separate the cells, especially those found on or near the surface of a sample, by the FTIR spectrum they produce. The sample may be any appropriate sample that may be obtained from a subject and that can be screened using FTIR, especially ATR-FTIR. In particularly, the sample may be a tissue biopsy, especially a sample of epithelial tissue. As is well known in the art, epithelial tissue means tissue taken from epithelium. It can include, for example, epithelial tissue from the circulatory system; the digestive system such as from the esophagus, the stomach and the intestines; the endocrine system; the integumentary system; the reproductive system; the respiratory system and the urinary system. In a particular example, the sample is obtained from the esophagus. When the sample is from the esophagus, it may include, for example, cells that have come from the squamous epithelium and/or from the lamina propria. The sample may be a tissue sample, such as a biopsy or resection, or may be any other sample that contains cells, such as a sample of bodily fluid, for example saliva, urine, blood, serum, csf, amniotic fluid, aqueous or vitreous humour, bile, or any other secretion. The sample may be obtained by any appropriate means, such as by swabbing, scraping, biopsy or needle sampling. The sample may be spun (centrifuged) prior to fixing on a slide. The sample may be removed from the body, or may remain in or part of the body, that is to say it may be ex vivo or in vivo, providing it can be accessed by an appropriate spectrometer.

The sample may be a fresh tissue sample obtained directly from the patient or may be stored. Depending on the sample in question, the fresh tissue sample may be stored for minutes or even hours. Alternatively, the sample may be treated. For example, the sample may be a sample that is, or has been (flash) frozen or which is on ice or it may be a sample that has been fixed, for example by formalin fixing (at room temperature). The sample fixed in formalin may then be embedded in paraffin and optionally deparaffinised, as needed. The method may comprise the step of any one or more of storing, freezing, flash freezing, thawing, drying, rehydrating, hydrating, fixing, embedding (in paraffin) or deparaffinising the sample. The method may also comprise the step of calibrating the sample so as to correct any changes that may have been brought about by the treatment of the sample, for example, correcting hydrating levels. The method may also comprise the step of calibrating for any drug or other pharmaceutical agent or for any other agent, such as a stain, that may have been administered to the subject prior to sampling. The drug or other pharmaceutical agent may be a topical agent, such as one comprising acetic acid, adrenaline, NAC (N-acetyl cysteine) or throat spray. The stain may be methyl blue or any other suitable stain.

The sample may be a sample of tissue expected or known to contain cancerous or precancerous cells. Alternatively, it may be a sample of tissue expected or known to contain other cell types, particularly diseased cell types.

The method may include the step of obtaining the sample, or the sample may have been previously obtained and the method practised entirely in vitro.

The method includes the step of providing the results of scanning the sample with an infrared spectrometer. Any appropriate spectrometer may be used, for example a bench-based spectrometer, or a probe. The spectrometer is preferably a FTIR spectrometer, more preferably an ATR-FTIR spectrometer. The method may include the step of scanning the sample, or may simply comprise or consist of the steps of analysing the results of the scan.

The method comprises the step of separating the cells according to the spectra they produce. The spectral range produced by the cells typically falls within the 1800-600 $cm^{-1}$ region. The separating step may be carried out by comparing the spectra produced by the cells in the sample with the spectra produced by known cells. Alternatively, or additionally, the step may be carried out by comparing the spectra produced by the sample with expected spectral peaks. The term expected spectral peak is used to mean the peaks expected to be found on spectra obtained from known cells. The inventors have created a library of spectra from samples of known cells, the cells being identified by standard histological techniques. A library such as this can be used to provide spectra or expected spectral peaks with which the sample spectra may be compared. The method may include the step of obtaining spectra from known cells, or this may be carried out separately. The spectra of the known cells and of the sample should be obtained from the same type of spectrometer.

The method comprises the step of separating the cells into their varying types or classes. In particular, the method may comprise the step of separating the cells into healthy and non-healthy cells, i.e. differentiating or sorting between those cells that produce the spectrum associated with healthy, especially non-cancerous cells, and those that produce different spectra. Non-healthy cells may be any cells that do not produce a healthy cell spectrum. They may be cells that are diseased or may simply be cells that do not produce a healthy cell spectrum. In particular, non-healthy cells may include, for example, cancerous and pre-cancerous cells such as those found in squamous cell carcinoma, lung cancer, prostate cancer, breast cancer, cervical cancer and more, or cells that are associated with the presence of inflammation such as those found in Inflammatory Bowel Disease (IBD) or Inflammatory Bowel Syndrome (IBS). The non-healthy cells may also include cells from other diseases or disease states such as *H. pylori* infection, stomach ulcers, Crohn's disease, celiac disease, ulcerative colitis and more. It is useful to be able to differentiate between healthy and non-healthy cells, as a sample containing only healthy cells can be declared healthy, without the need for further histological analysis.

Alternatively, the method may be for confirming whether a sample contains viable cells. The method may also be useful for confirming that a sample has been taken from the correct location, by, for example, confirming the presence of particular cell types that should be at that location. It is possible to sort the sample by spectrum to identify whether the sample contains particular cells or not, or to identify whether the sample contains living cells, dead or dying cells, a combination of those, or no cells at all. Accordingly, there is provided a method for identifying the presence of cells within a sample, comprising the steps of providing the spectra produced by scanning the sample using FTIR spectroscopy; and identifying cells in the sample according to the spectrum each produces. Alternatively, or additionally to any previously mentioned step, the method may comprise the step of separating different cell types. Samples usually contain more than one cell type. For example, a sample of esophageal epithelium will usually comprise at least some squamous epithelial cells and some lamina propria cells. It can be particularly useful to be able to differentiate between cell types, especially if the sample is being examined for a disease of a specific cell type. If that cell type is not present, the sample can be discarded.

Alternatively, or additionally to any previously mentioned step, the method may comprise the step of separating cells by disease or disease state. For example, the method may comprise the step of separating cancerous and pre-cancerous cells from each other and/or from other cells in the sample. The method may comprise the step of sorting between healthy cells and those cells containing or acting as markers of carcinogenesis in another part of the body (remote carcinogenesis). For example, if the sample being examined is esophageal epithelium, the method may comprise separating non-dysplastic Barrett's esophagus (NDBE) cells from cells with low-grade dysplasia (LGD), high-grade dysplasia (HGD) and then esophageal adenocarcinoma (EAC). The cells may also be sorted by other diseases or disease states including cells involved with or showing evidence of inflammation, such as those found in Inflammatory Bowel Disease (IBD) or Inflammatory Bowel Syndrome (IBS), other cancer types, including squamous cell carcinoma, lung cancer, prostate cancer, breast cancer, cervical cancer and more. The cells may also be sorted by other diseases or disease states including *H. pylori* infection, stomach ulcers, Crohn's disease, celiac disease, ulcerative colitis and more. The cells may also be sorted by, for example, species type.

The cells may be separated by type or class, as described as above. Each separation step may be used, either on its own, or in conjunction with another step. The separation steps may be used in any order and may be repeated. In one embodiment, the step of separating healthy and non-healthy cells is carried out before other separation steps. In one embodiment, the step of separating the cells by type is carried out before separating the cells by disease state. In one embodiment, the separation steps are carried out in the order: healthy or non-healthy; cell type; disease state.

The method may also include generating an image of the sample.

Following any step of separating the cells into different classes or types, one or more of the classes or types can be removed from the image of the sample generated by the spectrometer. It is therefore possible to provide an image showing the presence or absence of a selected cell type or class or group of types or classes, i.e. those not removed from the image.

The method may also include the step of shifting or calibrating the spectra to take into account the hydration of the sample. Drier samples may produce different spectra to wet samples. The effect of the sample's hydration may be predicted though and taken into account. The method may also comprise the step of calibrating for any drug or other pharmaceutical agent or other agent, such as a stain, that may have been administered to the subject prior to sampling. The drug or other pharmaceutical agent may have been topically administered, such as any drug or pharmaceutical agent comprising acetic acid, adrenaline, NAC (N-acetyl cysteine) or throat spray. The stain may be methyl blue or any other suitable stain.

Any other factors that may affect the spectra may be accounted for in a similar manner.

The separation, shifting and/or image generation steps of the method may be carried out by way of a computer programmed to or having a programme installed to carry out some or all of these steps.

The method includes the step of screening or scanning the sample with a spectrometer. The sample may be scanned once, or more than once, so as to provide the best possible image. The sample is often a slice of tissue, having a top and a bottom. When this is the case, it may be scanned on both sides, or just on one side. Other samples may be scanned differently according to their shape and size. For example, if the sample (or any side of the sample) is larger than the prism (3 mm/3 mm), it may be necessary to scan two or more places on the same side. Advantageously, it is also possible to detect distant disease in a sample even if the region scanned is not diseased. A skilled person will be able to determine the appropriate size (for example, area and thickness) and shape limits of samples suitable for detecting a distant disease.

The sample may be flattened or held on a slide in order to allow the best scan. The sample may also be treated prior to scanning, such as wetted or dried.

According to a second aspect of the invention, there is provided a computer programme comprising code means to carry out at least one of the separation, shifting and image generation steps of the invention. Further provided is a computer readable medium comprising such a computer programme. Further provided is a system, comprising a computer enabled to run the computer programme, for example the programme being installed on the computer or on a server to which the computer is connected. The system may also comprise a spectrometer. The system may also comprise a library of spectra from known cells, which may be accessed by the computer for use in the separation step.

A third aspect of the invention provides a method for diagnosing a disease state in a subject, comprising analysing the results of an infrared spectroscopy scan of the sample and identifying or separating the cells in the sample according to the spectra they produce. The disease state may be any disease that causes a cell to produce a different spectrum to a healthy cell of the same type. In particular, the disease state may be cancer or a pre-cancerous state, especially cancer of an epithelial tissue, especially BE or EAC.

BRIEF DESCRIPTION OF THE SEVERAL VIEWS OF THE DRAWINGS

The invention will now be described by way of example only, with reference to the drawings.

FIGS. 3A, 3B and 3C show: A) A 3 µm thick H&E stained cross section of an HGD biopsy sample, where the area marked with a blue line indicates HGD features defined by a histopathologist. B) An adjacent FTIR image of 8 µm section colored by the first two groups of a HCA of the 1610-1530 $cm^{-1}$ spectral region where epithelium is blue and contains 1271 pixels and lamina propria is red 1882 pixels. Black pixels are those with an amide II with an absorbance less than 0.05. C) The average absorbance (top) and second derivative (bottom) spectra from the HCA classes.

FIGS. 4A, 4B and 4C show: A) A 3 µm thick H&E stained cross section of an EAC resection. B) An adjacent FTIR image of 8 µm section colored by the first two groups of a HCA of the 1610-1530 $cm^{-1}$ spectral region. The blue contains 1247 pixels and red contains 1901 pixels. Black pixels are those with an amide II with an absorbance less than 0.05. C) The average absorbance (top) and second derivative (bottom) spectra from the HCA classes.

FIGS. 5A and 5B show the average absorbance (top) and second derivative (bottom) spectra comparing A) SQ epithelium versus all other BE stages and B) manually selected from regions of NDBE, LGD, HGD+ and EAC in A) the 1800-1000 $cm^{-1}$ region and B) the 1300-1000 $cm^{-1}$ spectral region.

FIGS. 6a and 6B show the average absorbance (top) and second derivative (bottom) spectra comparing A) SQ lamina propria versus all other the average of NDBE/LGD/HGD+ lamina propria and EAC and B) manually selected from regions of NDBE, LGD, HGD+ lamina propria and EAC in A) the 1800-1000 $cm^{-1}$ region and B) the 1300-1000 $cm^{-1}$ spectral region.

FIG. 7 is schematic illustrating how single element ATR-FTIR spectra were separated first into SQ and NDBE/HGD/EAC groups (i), then into their predominant tissue types present, either epithelium or lamina propria (ii), before classifying into their respective disease classes: either NDBE EP (epithelium) or HGD EP (epithelium)/EAC (iii a); or, NDBE LP (lamina propria) or HGD LP (lamina propria)/EAC (iii b).

FIGS. 8A and 8B show: A) Mean absorbance (top) and second derivative (bottom) spectral differences between 61 SQ epithelium (green), 106 SQ lamina propria (blue) and 616 NDBE/HGD/EAC (black) biopsy spectra between the 1800-850 $cm^{-1}$ region. B) Scores plot of the 3 latent variables (LV) used in the PLSDA of the 1385-1235 and 1192-1130 $cm^{-1}$ SQ versus NDBE/HGD/EAC model. Each point refers to one of the 167 SQ or 543 NDBE/HGD/EAC biopsy spectra.

FIG. 9 shows the absorbance (top) and second derivative (bottom) spectral differences between the mean of 368 NDBE/HGD/EAC epithelium spectra (blue) and 175 NDBE/HGD/EAC lamina propria spectra (red) after separation into the predominant tissue type present.

FIGS. 10A and 10B show: A) Mean absorbance (top) and second derivative (bottom) spectral differences between 271 NDBE (blue), 115 HGD epithelium/EAC (red) biopsy spectra between the 1300-870 $cm^{-1}$ region. B) Scores plot of the first two latent variables (LV) out of the 4 LVs used in the PLSDA model of the 1100-900 $cm^{-1}$. Each point refers to one of the 198 NDBE epithelium biopsies or 66 HGD epithelium/EAC biopsies. If more than one spectrum was present for a single biopsy, the scores were averaged.

FIGS. 14A, 14B, 14C and 14D show the FTIR Spectra from bronchial epithelium at different disease stages. Fifteen regions were selected with the following disease stages: areas 1-3, healthy; 4-6, mild dysplasia, areas 7-9, moderate dysplasia and areas 10-15, severe dysplasia/carcinoma in situ. The areas were colour coded according to the size of the A) 1036 $cm^{-1}$ second derivative trough integral and B) the size of the 1163 $cm^{-1}$ second derivative trough integral. The Corrupt Data box present in A) and B) indicate two adjacent tiles of the FTIR image where the data recorded were corrupt and unusable. C) Shows the absorbance (top) and second derivative (bottom) spectra in the 1800-1000 $cm^{-1}$ spectral region, averaged from the 15 selected EP areas ranging from healthy to severe dysplasia/carcinoma in situ. D) The 1250-1000 $cm^{-1}$ spectral region.

FIGS. 17a and 17 B show FTIR Spectra from the manually selected regions of the bronchial lamina propria. A) Shows the absorbance (top) and second derivative (bottom) spectra in the 1800-1000 $cm^{-1}$ spectral region, averaged from 15 areas ranging from healthy (blue) to severe dysplasia/carcinoma in situ (red). B) The 1250-1000 $cm^{-1}$ spectral region of the same spectra. The position of the manually selected areas from LP can be seen in FIG. 16.

DESCRIPTION OF SPECIFIC EMBODIMENTS OF THE INVENTION

Methods

FTIR Spectroscopic Imaging

Figures 1A, 1B, 1C:
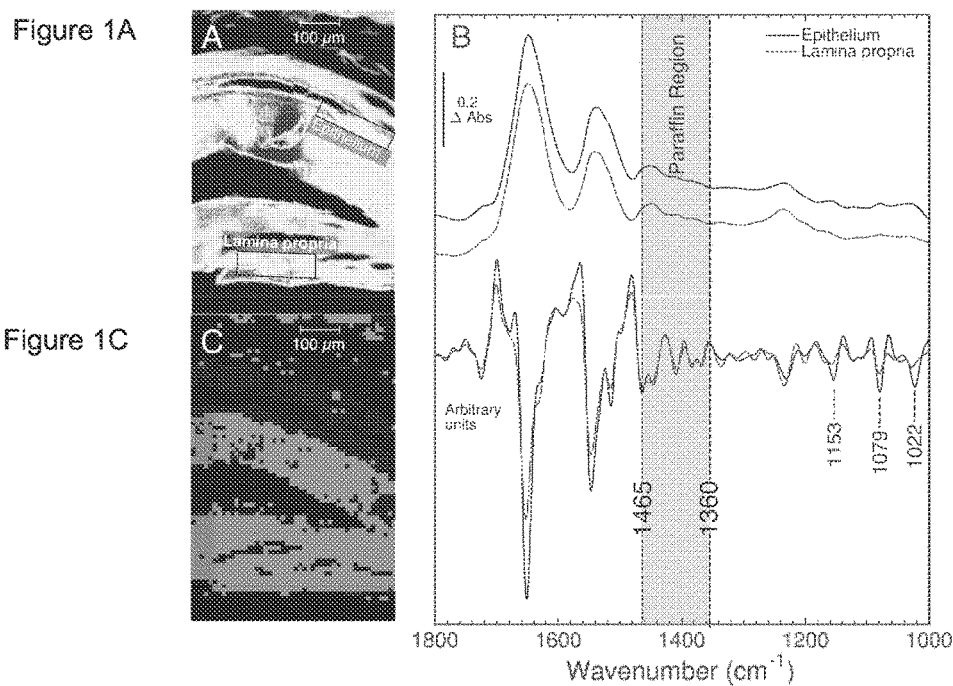
FIGS. 1A, 1B and 1C show: A) 2×4 FTIR image of an 8 µm thick SQ tissue section pseudo colored to the height of the amide II band from 1570 and 1485 $cm^{-1}$. The boxes represent areas selected from known epithelium and lamina propria tissue types. B) Absorbance (top) and second derivative (bottom) spectra co-added and averaged from the known tissue type regions. The epithelium (blue) contained 418 averaged spectra and the lamina propria 1777 averaged spectra. C) Pixels colored to the first two groups of a HCA of the 1200-1100 $cm^{-1}$ spectral region of a 4×4 binned image. Blue pixels correspond to the epithelium and red to the lamina propria. Black pixels are those with an amide II with an absorbance less than 0.05 and were not included in the HCA.

FTIR spectroscopic images were measured using a Bruker IFS 66 spectrometer coupled with a Hyperion IRscope II microscope with a 15×0.4 NA objective, and a 128×128 pixel mercury-cadmium-telluride focal plane array (FPA) detector. The use of an array detector allows spectra to be obtained simultaneously from different spatial regions of the sample and is significantly faster than mapping the same area with a single element Detector[34,38]. An NDBE/LGD and a SQ sample were microtomed to an 8 µm thickness and mounted on 2 mm thick calcium fluoride windows and deparaffinised by a standardized xylene protocol [reference].

Spectroscopic images were recorded using the FPA with a 96×96 pixel window, giving a field of view of 256×256 µm². Using in-house developed macros, spectral images were acquired from different parts of the tissue and combined in Matlab to produce large data sets. Each sample was mapped to cover an area containing regions of epithelial and lamina propria cell types as well as different levels of dysplasia, which were previously graded by histopathologists. The FTIR images were binned in 4×4 matrices to increase signal to noise. Any pixels that contained an amide II integral of less than 0.5 between 1571-1490 $cm^{-1}$ were excluded from further analyses. All other spectra were normalised to the height of the amide II peak and trough between 1555 and 1475 $cm^{-1}$. The images were subsequently binned in 4×4 matrices to improve signal to noise ratios. Contributions of water vapor were removed by the subtraction of a pre-recorded water vapor reference spectra. After processing, differences between different cell types were revealed.

ATR-FTIR Spectra Recording

A Bruker Optics IFS 66/s FTIR spectrometer that records in the region of 6000-800 $cm^{-1}$ was used to record spectra, however only the 4000-900 $cm^{-1}$ region was collected, however, only the 2200-900 $cm^{-1}$ region was analysed. The machine has a liquid nitrogen cooled MCT-A detector with an Attenuated Total Reflection (ATR) 3-reflection silicon prism with ZnSe optics. The spectra were recorded using the Bruker OPUS 6.5 software.

All measurements were recorded at 4 $cm^{-1}$ resolution, giving a peak accuracy of approximately ±1 $cm^{-1}$. 1000 background interferograms of the clean prism surface were averaged (taken after carefully cleaning the prism with water and 100% ethanol) and, after correct placing of the biopsy sample, 500 interferograms were averaged to produce single biopsy absorbance spectra.

Data Processing

All data was converted from Bruker OPUS 6.5 file format to ASCII file format from within the software. The data was then preprocessed and analyzed using in house scripts developed in MATLAB_R2012b and/or PLS toolbox v 7.0.3.

Prior to analysis, four data pre-processing steps were applied to each spectra; in this order: spectral water subtraction using a reference water spectrum, spectral water vapor subtraction using a pre-recorded reference spectrum, normalization to the height of the amide II band, and second derivative calculation.

Histopathology

The gastrointestinal department at UCLH had two associated histologists. To ensure a correct diagnosis, both histologists independently verified any sample with a dysplastic diagnosis. The samples were stored in a 4% formalin solution, placed in embedding cassettes, and dehydrated by placement in the following solutions of ethanol for 2 hours: 70%, 80%, 95% and 100% with each solution being refreshed after one hour. Biopsies were then placed in xylene for three hours, changing the solution every hour. The biopsies were then placed in paraffin wax (~57° C.) for 1.5 hours, and repeated before embedding into a paraffin block. Blocks were then sliced with a microtome into 4 µm sections in a 40-45° C. water bath, mounted on a glass slide and oven dried. The sample was then rehydrated in xylene for 5 minutes; the solution was changed and then repeated 3 times. The sample was then rinsed in 100% ethanol for three minutes, repeated, and followed by 3 minutes in 95% ethanol after which the sample was rinsed with distilled water and stained for inspection.

The samples were then categorized as either healthy SQ epithelial cells, or one of the three classes of BE; NDBE, HGD or EAC. In the case of the intercepted-matched dataset, an additional class of NDBE-IM was included. An expert pathologist at UCLH diagnosed each biopsy, and if a biopsy was diagnosed with either HGD or EAC, an additional histologist independently verified the diagnosis.

Biopsies classified as LGD were excluded from the training data of the model.

Statistical Analyses

Partial Least Square Discriminant Analysis

Partial least square discriminant analysis (PLSDA) was applied for dimensionality reduction to maximize the covariance between explanatory, correlated variables (wavenumbers) and categorical variables (disease stage). Since the model was built using a multi-step process, the subset of variables (wavenumbers) changed depending upon the cell type. For the SQ separation the 1385-1235 and 1192-1130 cm$^{-1}$ region was used, for the epithelium diagnostic model the 1200-900 cm$^{-1}$ was used and for the lamina propria 1290-1210 and 1130-870 cm$^{-1}$ region was used. These regions were then reduced into a lower dimensional space of uncorrelated variables, referred to as latent variables, the number of latent variables used are indicated within the results section. To calculate fast and accurate the PLS model, we follow the approach of De Jong, Sijmen[39].

Logistic Regression

In order to discriminate disease stages we assigned a probability to each stage based on the scores generated from the PLSDA using logistic regression analysis. The logistic regression model is given by $$\log\left(\frac{P(Y_i = 1|X^*)}{1 - P(Y_i = 1|X^*)}\right) = \beta_0 + X^*\beta$$

where $Y_i$ describes the binary responses (disease stages), $\beta_0$ is the intercept, $\beta$ is the vector of coefficients and $X^*$ is the matrix of latent variables. From this equation we can calculate the probabilities for each disease stage and a classification rule must then be applied in order to identify a threshold between the two groups.

Applying a Misclassification Cost

To optimize the classification performance we applied misclassification costs to the decision problem. Given the data, $X^*$, there were two possible decisions: No-treat, which corresponds to grouping an unknown biopsy spectrum as no-treat (SQ/NDBE) and treat, which corresponds to grouping an unknown biopsy spectrum as treat (HGD/EAC). No losses were applied to a correctly classified biopsy spectrum. If the decision was no-treat, but the true group was treat, then there is a cost of $\lambda_{treat}$, which was fixed at 1. Similarly, the decision misclassification of treat biopsy as no-treat was assigned a cost $\lambda_{no-treat}$, which was varied, refer to results section for $\lambda_{no-treat}$. See below:

$$\begin{pmatrix} 0 & \lambda_{treat} \\ \lambda_{no-treat} & 0 \end{pmatrix}$$

The conditional risks (expected losses) are r(no-treat|$X^*$)=$\lambda_{treat}$p(treat|$X^*$) and r(treat|$X^*$)=$\lambda_{no-treat}$ p(no-treat|$X^*$). The decision is no-treat, if r(no-treat|$X^*$)<r(treat|$X^*$), or equivalent $\lambda_{no-treat}$ p(no-treat|$X^*$)>$\lambda_{treat}$p(treat|$X^*$), otherwise the decision is treat.

Optimize the performance of the evaluation measurements by including an additional 'inconclusive' prediction class, which corresponds to the samples that, lie very close to the threshold (t). If G=|p(no-treat|$X^*$)$\lambda_{no-treat}$−p(treat|$X^*$)$\lambda$treat|<t, then the sample is characterized as 'inconclusive', where t in practice is selected the q %-quantile of these differences in absolute values. On the other hand, the decision either threat or no-treat is done with 100%−q % confidence, if G>t.

Cross Validation

In order to most closely represent the clinical environment, the training dataset and the test dataset never contain the same patients, regardless of the number of biopsies taken from each patient. The process is as follows, where N is the number of patients: i) the biopsies are randomly split into N, not necessarily of equal size, sub-samples, such that biopsies that referred to the same patients belong to the same sub-sample, ii) use N−1 sub-samples of patients as training data and one sub-sample, out of the N patient, as test data and iii) repeat first two steps N times, one for each patient. The method is not so computationally expensive since the number of patients is much lower than the number of biopsies.

Results

FTIR Imaging to Generate a Library of Cell and Disease States Spectral Characteristics The single element ATR-FTIR method, though rapid, simple and with high signal/noise, has several inherent limitations. One of these being the large field of view (several mm$^2$), which results in the averaging of spectra of all cell types and disease stages across a sample. This means that spectral differences between diseased and healthy cells are difficult to resolve. In particular, signals from a small number of diseased cells may be averaged out in a sample that is predominantly healthy. To overcome this limitation, FTIR imaging was used to generate a library of cell and disease stage characteristics. FTIR microspectroscopic images of 8 μm thick tissue sections containing known disease stages: SQ, NDBE with a LGD region, HGD and EAC were recorded. Characteristic features of cell types and disease stages could then be selected from these images and used to better identify spectral signatures of specific cell types in ATR-FTIR spectra.

Cell Type Spectral Characteristics of a SQ Biopsy Section

A SQ sample is expected to contain two tissue types: surface epithelium (EP) and underlying lamina propria (LP). FIG. 1A shows an FTIR image of an 8 μm thick tissue section of a SQ sample that was pseudo colored to the amide II band height. The boxes in FIG. 1A indicate known areas of EP and LP. Spectra from these two areas were co-added and averaged (FIG. 1B). The main differences between these averaged spectra occur in the 1200-1000 cm$^{-1}$ region. A hierarchical clustering analysis (HCA) was performed using this spectral region of the second derivative spectra. This produced two predominant groups that clearly corresponded to the SQ epithelium and lamina propria (FIG. 1C).

Cell Type Spectral Characteristics of a NDBE/LGD Biopsy Section

Figures 2A, 2B, 2C:
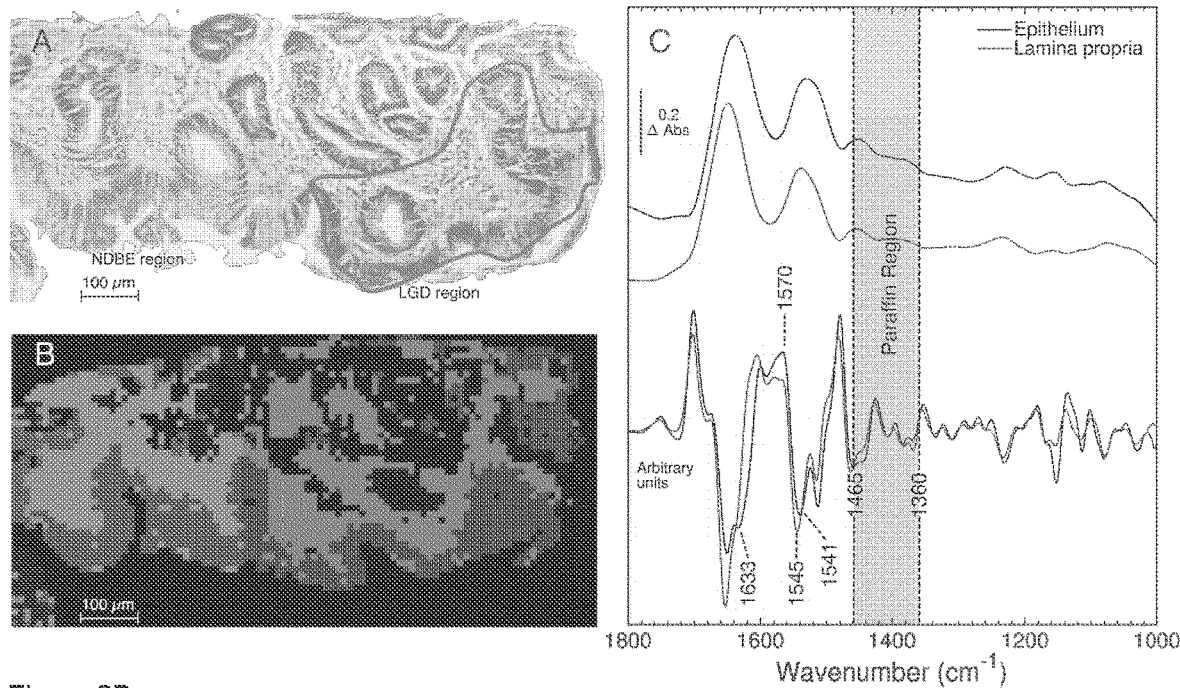
FIGS. 2A, 2B and 2C show: A) A 3 µm thick H&E stained cross section of an NDBE biopsy sample with a small region of LGD indicated by the region marked by a blue line. B) An adjacent FTIR image of 8 µm thick section, colored by the first two groups of a HCA of the 1610-1530 $cm^{-1}$ spectral region. The epithelium is colored in blue and contains 1494 pixels and lamina propria in red and contains 1266 pixels. Black pixels are those with an amide II with an absorbance less than 0.05, these data were not included in the HCA. C) The average absorbance (top) and second derivative (bottom) spectra from the HCA classes.

FIG. 2A shows a 3 μm thick tissue section that had been H&E stained for histological analysis. This sample was histologically defined as predominantly NDBE with an area of LGD. There are two main tissue types present in this sample: columnar epithelium (CEP) cells and LP. Spectra from known regions of CEP and LP were manually inspected and the largest differences between them occurred around the 1600 cm$^{-1}$ region. In order to classify all pixels from the image as either CEP or LP, a HCA was performed using the 1610-1530 cm$^{-1}$ region of the second derivative spectra. This produced two predominant groups that clearly corresponded to areas of CEP and LP (FIG. 2B). The averaged spectra from these two HCA classes are shown in FIG. 2C. There are several features, seen most clearly seen in the second derivative spectra, that show separation between the CEP and LP in this NDBE/LGD sample: a CEP peak at around 1570 cm$^{-1}$ that is absent in the LP spectra; a 4 cm$^{-1}$ shift of the amide II trough from 1541 cm$^{-1}$ in the CEP to 1545 cm$^{-1}$ in the LP; a change in the size of the 1633 cm$^{-1}$ shoulder of the amide I band, where the CEP amide I shoulder at 1633 cm$^{-1}$ is more prominent than in the LP; and there is an increase in the amide I/amide II intensity ratio of 0.27 from CEP to LP.

Cell Type Spectral Characteristics of a HGD Biopsy Section

FIG. 3A shows a 3 μm thick tissue section that was histologically defined as at least HGD (HGD+). Following the same tissue type separation approach as in the SQ and NDBE/LGD FTIR images, spectra from known areas of identifiable CEP and LP were manually inspected and similar differences around the 1600 cm$^{-1}$ region were seen. A HCA of 1610-1530 cm$^{-1}$ region was performed to separate all the pixels in the image into CEP or LP groups. As with the NDBE/LGD sample, two predominant HCA groups that corresponded to regions CEP and LP, could be seen (FIG. 3B). However, the differences between their averaged spectra (FIG. 3C) were not as pronounced as in the NDBE/LGD sample. There was only a small peak difference between the CEP and LP at 1570 cm$^{-1}$; a 2 cm$^{-1}$ shift of the CEP amide II band from 1542 cm$^{-1}$ to 1544 cm$^{-1}$ in the LP; a small 1633 cm$^{-1}$ amide I shoulder of the CEP spectra; and a smaller increase in the amide I/amide II intensity ratio of 0.18 from CEP to LP.

Cell Type Spectral Characteristics of a Large EAC Tissue Section

FIG. 4A shows a 3 μm thick section of a large (1 cm in diameter) piece of tissue that was histologically defined as EAC. This sample is a resection and is larger than the typical diameter of a biopsy sample (1-2 mm). An EAC sample of this size contains a fibrous layer of cells on the surface of the sample, and irregularly spaced invaginations of CEP and LP on the underlying side. This study is focused on the diagnosis of biopsies using ATR-FTIR spectroscopy, and if a biopsy, with the typical size of 1-2 mm, was taken from an EAC region, it is unlikely that it would contain a tissue type other than that of the fibrous layer. Therefore, only the outer edge of the EAC sample was imaged (indicated by the black box in FIG. 4A). It is expected that neither the CEP nor LP tissue types would be present in the fibrous layer. To check whether these tissue types with the same characteristics as in the NDBE/LGD and HGD samples were identifiable in this layer, a HCA using the same 1610-1530 cm$^{-1}$ spectral region was performed. A clear separation into two predominant groups was not achieved. A color map of the first two groups is shown in FIG. 4B, there is no clear separation into identifiable tissue types and the averaged spectra of these two groups (FIG. 4C) only showed weak and insignificant spectral differences.

Comparisons of Disease Stage Spectral Characteristics in the Epithelial Tissue

Although the NDBE, LGD and HGD+ CEP and the SQ EP are all epithelial cell types, they have different cell structures. Therefore, the spectral differences between CEP and SQ EP are expected to be larger than the spectral differences between disease stages of the CEP. FIG. 5A compares the SQ EP spectra taken from FIG. 1C with the average of NDBE/LGD/HGD+ CEP from FIGS. 2C and 3C. The most significant differences between the SQ EP and the CEP can be seen most clearly in the 1300-1000 cm$^{-1}$ region of their second derivative spectra (FIG. 5A). The most prominent changes that occur from SQ EP to CEP are as follows: an increase in intensity of the 1292 cm$^{-1}$ band; the reduction in intensity of the 1212 and 1201 cm$^{-1}$ bands; the reduction in intensity of the 1168 cm$^{-1}$ and an increase in intensity of the 1154 cm$^{-1}$ peak; the change in composition of the band around 1116 cm$^{-1}$; and distinct changes between the 1066 cm$^{-1}$ peak and 1034 cm$^{-1}$ trough.

FIG. 5B compares the averaged disease stages occurring within the CEP (NDBE, LGD and HGD+) and EAC fibrous region. The most significant spectral differences were between NDBE/LGD and HGD+/EAC, and are best seen in the second derivative 1300-1000 cm$^{-1}$ spectral region in FIG. 5B. Spectral features that indicate a transition from NDBE to EAC include the following in the second derivative spectra: an increase in intensity of the 1283 cm$^{-1}$ trough; a decrease in intensity of the 1158 cm$^{-1}$ trough; a change in size ratio between the 1154 cm$^{-1}$ and 1167 cm$^{-1}$ bands, the 1167 cm$^{-1}$ trough also shifts to 1170 cm at the HGD+/EAC stage; a shift from the NDBE trough at 1116 cm$^{-1}$ to 1119 cm$^{-1}$ at the LGD/HGD+ stage and then to 1123 cm$^{-1}$ at EAC stage.

Comparisons of Disease Stage Spectral Characteristics in the Lamina Propria

The SQ LP and the LP present in BE samples (NDBE/LGD/HGD+) are expected to contain the same tissue components and therefore have similar spectra. FIG. 6A compares the SQ LP with the average of the LP from NDBE, LGD and HGD+ and the EAC spectrum. As expected the SQ LP and BE LP spectra are alike, however there are features that can be used to distinguish between them. These can be seen clearly in the second derivative: an increase in the intensity and a shift of the 1157 cm$^{-1}$ trough to 1153 cm$^{-1}$; an additional component in the BE lamina propria at 1114 cm$^{-1}$; and a reduction in the 1122 cm$^{-1}$ trough.

FIG. 6B compares the averaged disease stages occurring in the BE LP (NDBE, LGD and HGD+) as well as the EAC fibrous region. There are several spectral features that change during the progression of NDBE to EAC, which can be seen clearly in the second derivative 1300-1000 cm$^{-1}$ region, and include the following: the NDBE trough at 1233 cm$^{-1}$ initially shifts to 1232 cm$^{-1}$ at LGD, then decreases in intensity at HGD+, followed by a further shift to 1230 cm$^{-1}$ at EAC; the 1215 cm$^{-1}$ and 1053 cm$^{-1}$ bands decrease in intensity as BE progresses; the NDBE 1114 cm$^{-1}$ trough shifts through 1119 cm$^{-1}$ at HGD+ to 1122 cm$^{-1}$ at the EAC stage; the NDBE band at 1080 cm$^{-1}$ decreases in intensity and shifts through 1079 cm$^{-1}$ at LGD stage to 1077 cm$^{-1}$ at HGD+/EAC stage; and the band around 1045 cm$^{-1}$ decreases in intensity.

Single Element ATR-FTIR Spectroscopy of Fresh Biopsies In total, 790 biopsy spectra of 414 biopsies from 131 patients were measured using single element ATR-FTIR spectroscopy. Where possible, at least one spectrum was recorded of each side of the biopsies. In cases of small biopsies, only one spectrum was recorded; conversely if the biopsy was large, multiple spectra of each side were taken. The spectra were corrected for water and water vapor contributions, normalized to the height of the amide II band and converted into their second derivative forms before further analyses. Of these 790 spectra, 80 were removed as outliers, leaving a total of 710 biopsy spectra from 379 biopsies and 122 patients (Table 1). A spectrum was determined as an outlier if it deviated from the mean plus or minus the standard deviation in over 75% of the 1800-850 cm$^{-1}$ spectral region, after processing.

Grouping Biopsy Spectra by Predominant Cell Type

A further limitation to single element ATR-FTIR spectroscopy is the limited depth of penetration (several microns) of the evanescent wave[37], which means that only the surface layers of cells are analyzed. Biopsy samples tend to be roughly disc-shaped, with one face derived from the exposed surface (either SQ EP or CEP) and the other from the underlying tissue (LP). To help overcome the depth of penetration limitation, and because these two surfaces contain different cell types, spectra from both sides of the biopsy were routinely recorded and categorized according to their predominant cell type, before being analyzed by their disease stage.

The following predominant cell types were assumed to be present: EP or LP for SQ, NDBE and HGD; and EAC only for the fully cancerous samples. LGD samples have been purposefully removed from the training data of the model described here. This is because the inter-observer agreement of LGD diagnosis between histologists is low, where κ-values are reported as low as 0.27[8], and there is also debate over whether these patients should be treated with ablative therapies or not[4]. For these reasons LGD patients were excluded from the main part of the analyses. However, the ability of the model to predict these patients will be discussed.

In order to optimize the performance of the classification model, the spectra were sorted by the pipeline as illustrated in FIG. 7: (i) spectra were firstly assigned as either NDBE/HGD/EAC or SQ; (ii) the NDBE/HGD/EAC spectra were then separated into EP or LP tissue types; spectra in the (iii a) epithelium or (iii b) LP groups were then further separated into NDBE or HGD/EAC disease stages using additional misclassification costs. In the final step, spectra from either side of the biopsies were combined to give an overall biopsy prediction of either SQ/NDBE, a group that would clinically not require treatment, HGD/EAC, a group of patients that would require treatment or, inconclusive, where there was insufficient data to provide a conclusive disease class prediction.

(i) Separation of NDBE/HGD/EAC From SQ Biopsies

To effectively separate the SQ (SQ EP and SQ LP) tissue from all other disease stages (NDBE/HGD/EAC), a PLSDA with leave-one-patient-out cross validation was applied to the 1385-1235 and 1192-1130 $cm^{-1}$ spectral regions of 710 individual spectra. This spectral region was selected based upon the differences between the SQ EP and SQ LP comparisons in FIGS. 5A and 6A. Since it is more important to correctly classify a NDBE/HGD/EAC biopsy correctly, a NDBE/HGD/EAC misclassification cost of 3 was assigned to this class. The corresponding confusion matrix is shown in Table 2 and the spectral differences between SQ and NDBE/HGD/EAC can be seen in the averaged spectra shown in FIG. 8A. FIG. 8B shows the latent variables (LV) scores plot for this model where a good separation of the two can be seen. The sensitivity for detecting NDBE/HGD/EAC biopsies was 99% (536/543) with a specificity of 64% (107/167).

The specificity of the SQ detection model was low at 64%. Before continuing to the next step, information from the FTIR image study was used to help improve the performance of the model. SQ EP was found to have a unique band at 1153 $cm^{-1}$. The average integral of this group was $-5.6483 \times 10^{-5} \pm 0.15987 \times 10^{-5}$ and the average integral of all other tissue types/disease stages was $-0.0015 \pm 6.4367 \times 10^{-4}$. Therefore, if the integral of this component was less than or equal to $-8.5633 \times 10^{-4}$ it was classified as SQ EP. If a biopsy had a spectrum present in the NDBE/HGD/EAC and the SQ group, the SQ spectrum was checked for the presence of the unique SQ EP peak. If the peak was present the previously misclassified NDBE/HGD/EAC spectrum, was then re-classified as SQ. This additional check resulted in the correct re-classification of 28 of the 60 incorrectly classified SQ, improving the specificity of NDBE/HGD/EAC versus SQ model to 81% (135/160) without misclassifying any of the NDBE/HGD/EAC biopsies.

(ii) Separation of Epithelium From Lamina Propria in NDBE/HGD/FAC Spectra

The NDBE/HGD/EAC spectra were then analyzed in terms of whether they represented predominantly EP or LP cell types. FTIR imaging revealed that spectra from the EP could be distinguished from the LP of NDBE and HGD by the presence of a second derivative peak at 1570 $cm^{-1}$, and a shift of the amide II band. Based on this, k-means clustering analysis where k=2 (two groups), was performed on the 1610-1465 $cm^{-1}$ region of NDBE and HGD single element ATR-FTIR measurements. The 1610-1465 $cm^{-1}$ spectral differences between the EP and LP of NDBE and HGD samples were used to build a leave-one-patient out PLSDA model that would predict sidedness. FIG. 9 shows the average of the EP and LP predictions of all spectra from the NDBE, HGD, and EAC groups after the application of the model.

(iii a) Disease Stage Separation in Epithelial Spectra

After the separation of the NDBE/HGD/EAC spectra into EP and LP, these categories were further separated into NBDE or HGD/EAC disease stages. FIG. 10A shows the average spectra from those EP samples that had been histologically classified as NDBE or HGD/EAC. The spectral differences between NDBE and HGD/EAC are small. The 1200-900 $cm^{-1}$ spectral region, particularly bands at 1082, 1043, and 974 $cm^{-1}$, exhibited the largest differences between these disease stages. However, there was overlap between their standard deviations, which prevented the use of these bands as stand-alone classification features. Instead, a four latent variable, leave-one-patient out PLS model of the 1100-900 $cm^{-1}$ spectral region was built. FIG. 10B shows the PLS scores from the first two latent variables used to classify NDBE and HGD/EAC biopsies. PLSDA followed by logistic regression was performed on these PLS scores, and a misclassification cost of 3 was assigned since it is more important to correctly classify a HGD/EAC biopsy correctly. With the application of these costs a HGD/EAC sensitivity of 86% (71/83) and a specificity of 72% (221/308) was achieved. These model performance indicators include the 28 (out of 32) incorrectly classified SQ spectra from step (i) that subsequently entered this step in the model. However, it is important to note that these spectra were excluded from the training data as these spectra should not have been classified into this group. A SQ spectrum was incorrectly classified if identified as HGD/EAC and correctly classified if identified as NDBE. This is because the prediction classes that we initially defined were SQ/NDBE (no treatment required) versus HGD/EAC (treatment required).

(iii b) Disease Stage Separation in Lamina Propria Spectra

Figures 11A, 11B:
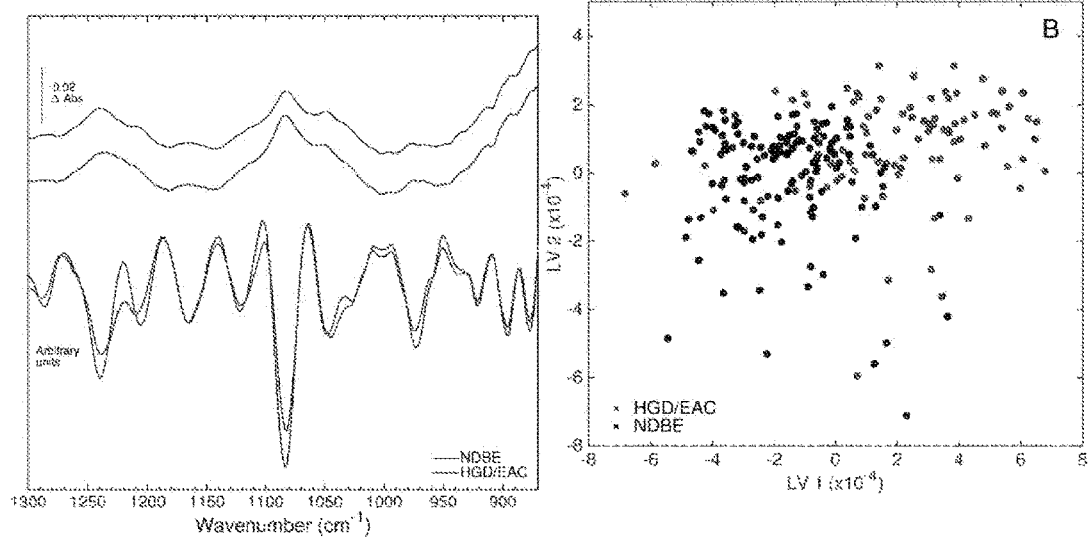
FIGS. 11A and 11B show: A) Mean absorbance (top) and second derivative (bottom) spectral differences between 141 NDBE lamina propria (blue), 89 HGD lamina propria/EAC (red) biopsy spectra between the 1300-870 $cm^{-1}$ region. B) Scores plot of the first two latent variables (LV) out of the 4 LVs used in the PLSDA model of the 1290-1210 and 1130-870 $cm^{-1}$. Each point refers to one of the 207 SQ/NDBE lamina propria biopsies or 53 HGD lamina propria/EAC biopsies. If more than one spectrum was present for a single biopsy, the scores were averaged.

FIG. 11A shows the average spectra from those LP samples that had been histologically classified as NDBE or HGD/EAC. The main spectral differences were seen in the 1290-1210 and 1130-870 $cm^{-1}$ regions, with the 1221 and 1047 $cm^{-1}$ bands showing the largest differences. Combinations of peak positions and integrals were not able to sufficiently separate the disease stages, therefore a two group (NDBE versus HGD/EAC) four latent variable PLS model of the 1290-1210 and 1130-870 $cm^{-1}$ region was built, with a HGD/EAC misclassification cost of 3. FIG. 11B shows the PLS scores from the first two latent variables. PLSDA was subsequently used to classify the PLS results. Although complete separation of the two groups was not achieved, identification of HGD/EAC had a sensitivity of 93% (41/43) and a specificity of 71% (95/133). These model performance indicators include the 7 (out of 32) incorrectly classified SQ spectra from step (i) that subsequently entered this step in the model. As in (iii a) these spectra were excluded from the training data, and a SQ spectrum was incorrectly classified if they was identified as HGD/EAC and correctly classified if identified as NDBE.

Combining Classification Results from Each Side of the Biopsy

As stated, where possible each biopsy had a total of two spectra recorded, one from each side of the biopsy. Of the 340 total biopsy ATR-FTIR measurements of BE EP and BE LP (not including EAC), 158 of them had one EP and one LP spectrum, 96 had two EP readings, 40 had two LP readings, 23 had only a single EP spectrum and 23 had only a single LP spectrum. Of the multiple spectra recorded, results from the various models agreed on average 87% of the time. After averaging the prediction scores, the sensitivity of the SQ/NDBE versus HGD/EAC was 90% and the specificity was 71% where the HGD/EAC misclassification cost was 3.

Optimizing the Model for Clinical Application

The sensitivity and specificity of the model described above can be further optimized to meet clinical needs in order to be used as a dysplastic BE biopsy screening device to aid the clinician's decision making process. A screening device requires a minimum sensitivity of 95%, where specificity can be sacrificed as long as there is a clear clinical benefit. To increase the sensitivity of this model an 'inconclusive' classification result was included. This step was used to improve the certainty of the two classes by reducing the number of false negatives and false positives in a single step. An inconclusive result was given if any of the following statements were true. First, the classification predictions from either side of the biopsy disagreed. Secondly if both of the cost adjusted p-values were above, or alternatively both spectra below a threshold of 0.8; meaning that if the model was certain that both spectra should fall into opposing classification groups, or alternatively if the model was uncertain that both spectra should fall into opposing classification groups, then the biopsy should be inconclusive. In the event that one spectra was above the threshold and the other was below the threshold, the biopsy would take the classification of the spectra above the given threshold. The inclusion of these rules resulted in an overall HGD/EAC sensitivity of 97%, a specificity of 83% and an inconclusive rate of 18%.

To test how the diagnostic model would perform for LGD patients, 27 spectra of 14 biopsies from 10 LGD patients were tested. After combining the predictions from both sides of the spectra as described above, 7 biopsies were classified as SQ/NDBE (where 2 were SQ); 2 were HGD/EAC and 5 were inconclusive. The inconclusive rate for LGD biopsies was 36%, higher than the inconclusive rate of 18% for the other classes.

Discussion

Here, we describe a technique that enables single element ATR-FTIR spectroscopy to be used as a real-time point-of-care screening device for HGD/EAC biopsies. Like other vibrational spectroscopic methods, ATR-FTIR spectroscopy can provide a clinical tissue diagnosis based on its biochemical profile. Where other methods try to offer an in vivo diagnostic that has a high initial cost and a requirement for a specialist operator, we suggest a more simplistic approach that can be operated by a nurse. One of the major benefits of single element ATR-FTIR spectroscopy is that is not limited to a single sample type, and no damage are caused to the samples. Therefore, it can be used for analysis of solids or liquids and the same sample can be sent on for classical diagnosis if needed, thus making it a versatile tool and applicable to many different clinical settings.

Biochemical changes between SQ, NDBE and HGD/EAC tissue can be seen in the 1200-900 $cm^{-1}$ spectral region, particularly the 1082, 1043, and 974 $cm^{-1}$ bands of the EP and the 1290-1210 and 1130-870 $cm^{-1}$ regions in the LP. These biochemical changes were modeled via PLSDA using a leave-one-patient-out cross validation built with 710 ATR-FTIR spectra of 379 fresh biopsies from 122 patients. There were three possible outcomes: SQ/NDBE, or no treatment required; HGD/EAC, where immediate treatment would be required; or inconclusive where the certainty of the result is not high enough to classify it. Each result had an associated certainty level (p-value), which could be displayed to the clinician in order to aid the clinical decision making process. The model has an overall accuracy of 90%, with a sensitivity of 97%, a specificity (not including inconclusive results) of 83% and an inconclusive rate of 18%. When the model was tested on LGD patients, 50% of the 14 biopsies from 10 patients were classified as SQ/NDBE, 14% were classified as HGD/EAC and 36% were inconclusive. Ideally all LGD biopsies would either fall into the inconclusive or HGD/EAC. However, the model was trained using histology results for which the inter-observer agreement was less than 50% for LGD diagnosis. Therefore it was expected that the model would not classify LGD biopsies consistently into a single group. It is however encouraging that 36% of the results were inconclusive as LGD is a dysplastic stage between the NDBE and HGD/EAC classes. With more samples it would be possible to include an additional LGD group into the model.

If a spectrometer were to be installed with the model that we have presented here, a reduction of histological bulk by at least 50% could be achieved by only sending those biopsies with an uncertain prognosis for further analysis. This is based on the fact that over 90% of all Barrett's surveillance biopsies sent to histopathology are healthy. A reduction of histological bulk of this size would make considerable cost savings to the healthcare provider. Furthermore, there is potential for this model to provide benefit to those patients predicted to be HGD/EAC. When a patient is predicted to be HGD/EAC, the model is 83% certain that this is true. If the clinician assessed this p-value, and agreed with this prediction based on what they see at endoscopy and the patient's clinical history, there is potential for the patient to be treated immediately.

The study was conducted using a liquid nitrogen cooled single element ATR-FTIR spectrometer, which is not appropriate for use in the clinic. However, there are portable, room temperature devices available that claim to produce the same data quality as lab grade equipment in less than 10 seconds. In order to translate this device into the clinic, a larger study would need to be conducted on one of these smaller benchtop single element ATR-FTIR spectrometers.

Application of FTIR Imaging and ATR-FTIR Spectroscopy to Lung Cancer Diagnosis

FTIR imaging and ATR-FTIR spectroscopy as described above were also applied to lung cancer. FTIR spectroscopic imaging in transmission mode was used to characterise cell and disease progression of lung squamous cell carcinoma (SCC) in a single, deparaffinised, 8 µm thick biopsy section that contained histologically-defined areas of disease progression. Disease stages that were present in this biopsy included healthy, mild/moderate/severe dysplasia and SCC in situ. The use of such a sample was to eliminate inter-sample and inter-patient spectral differences that might occur that are unrelated to carcinogenesis and due to it being rare for a single sample to display a complete disease transition from healthy to carcinoma in situ. The present study describes for the first time FTIR spectroscopic imaging of such a sample. The cell type information gained from the FTIR image was used to develop an algorithm to sort a small dataset of fresh lung biopsies from 21 patients. Their disease stage differences were then assessed.

Use of FTIR Imaging to Characterize Spectral Features of a Bronchial Biopsy

Cell Type Differences

Figure 12A:
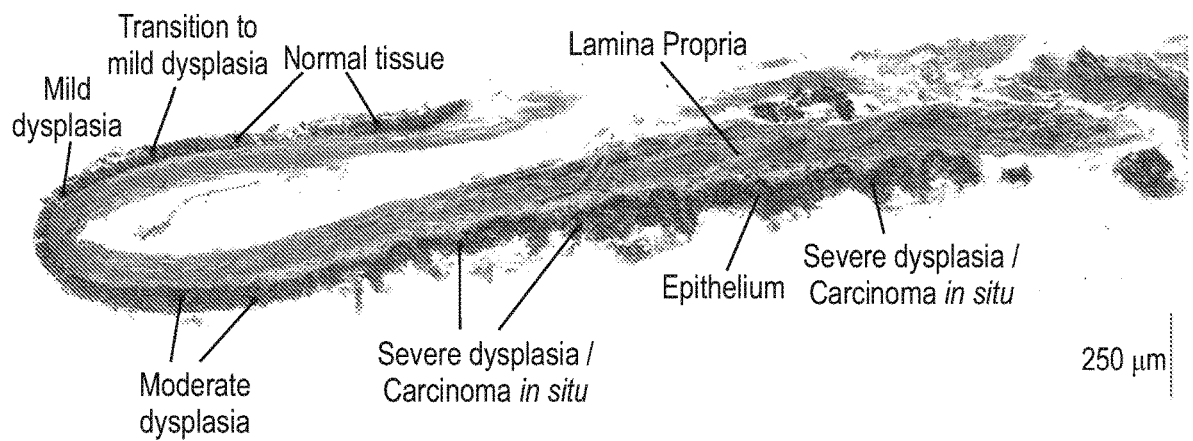
FIGS. 12A, 12B, 12c, 12D and 12E show the cell types and disease stages of a bronchial biopsy section. A) Histopathological analysis of the H&E stained section of the bronchial sample. B) Extracted spectra showing the absorbance (top) and second derivative (bottom) spectra of the EP and lamina propria, derived by averaging the HCA-defined regions of E). The grey area indicates the region in which paraffin absorbs. C) Heat map that shows EP (blue) and LP (yellow/red) separated on the size of the integral of the 1591 $cm^{-1}$ trough. D) Heat map that shows EP (red) and LP (yellow/green) separated on the size of the integral of the 1334 $cm^{-1}$ trough. E) Diagrammatical representation of the two major groups identified in the HCA of the 1614-1465 $cm^{-1}$ region, showing EP (red) and lamina propria (green). The Corrupt data box present in C), D) and E) indicate two adjacent tiles of the FTIR image where the data recorded were corrupt and unusable.
Figure 12B:
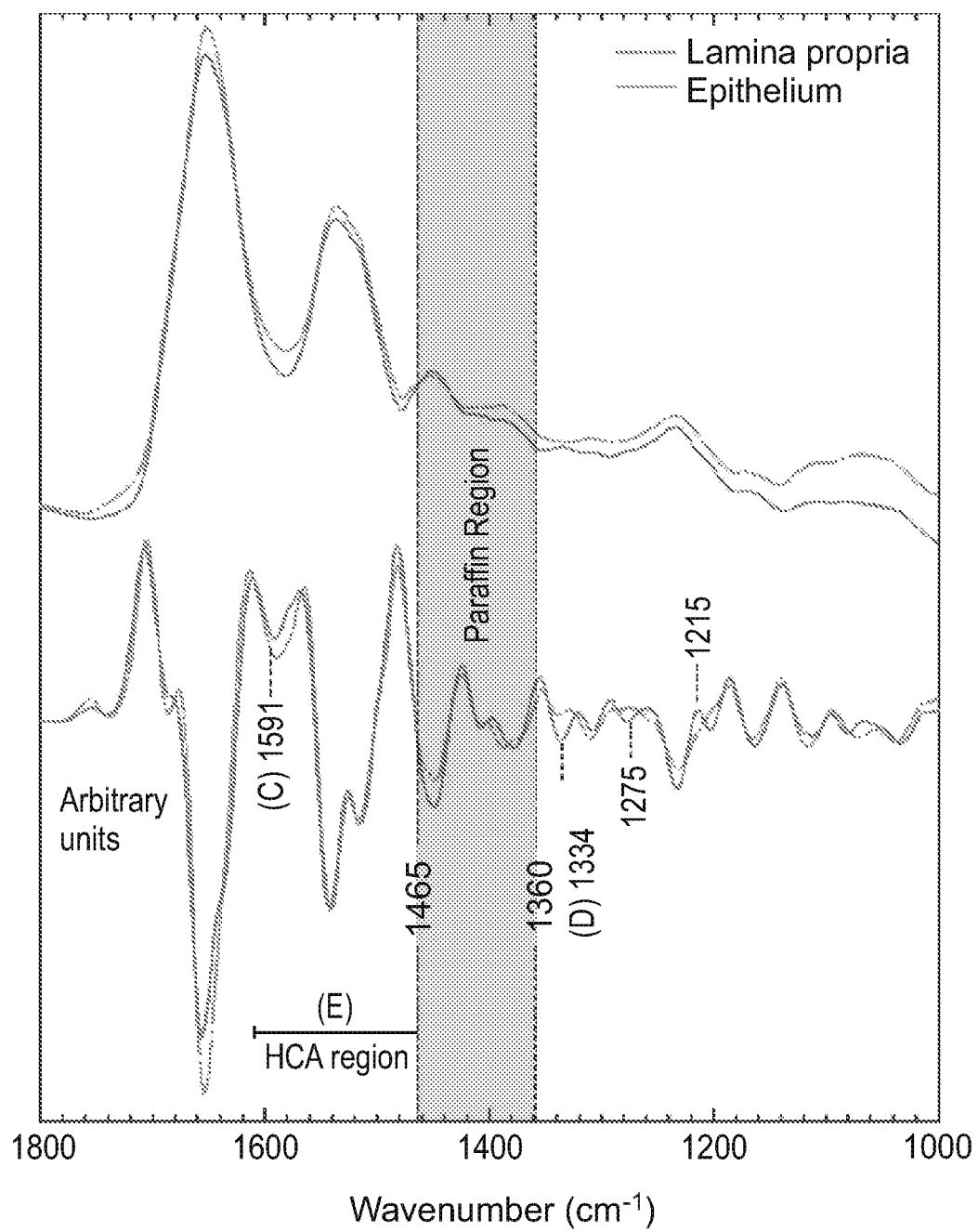
Figure 12C:
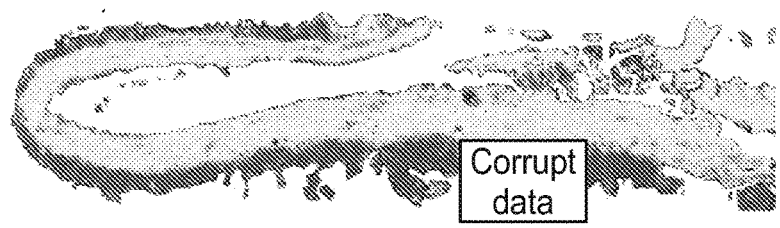
Figure 12D:
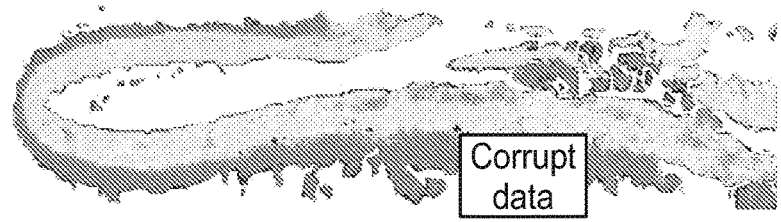
Figure 12E:

The largest spectral differences appear to be found between the cell types within a tissue. Therefore, in this study, the cell types were first separated before assessing disease stage differences within the cell types. FIG. 12 identifies cell types and disease stages of a bronchial biopsy section. FIG. 12A shows the H&E stained section of a 3 μm thick lung sample, together with the histologically defined regions of EP and LP, including the areas of epithelial disease stage progression. The disease progressions are marked by mild, moderate and severe forms of dysplasia as opposed to LGD and HGD. Mild dysplasia was equivalent to LGD, and severe dysplasia was equivalent to HGD.

Figure 13:
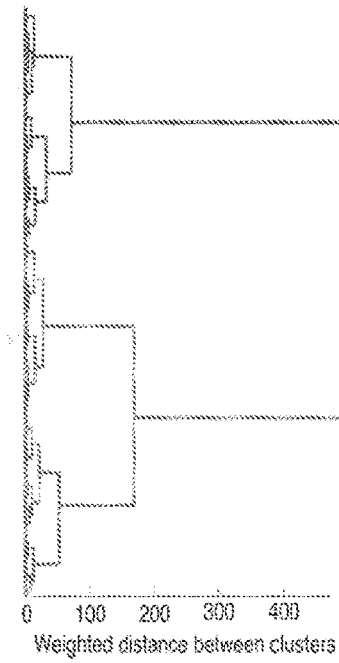
FIG. 13 is a dendrogram separating cell types of the bronchial biopsy. HCA of the 1614-1465 $cm^{-1}$ region.

FIG. 13 shows a dendrogram separating cell types of the bronchial biopsy. HCA of the 1614-1465 $cm^{-1}$ region. The spectral differences between the bronchial surface EP and the underlying LP are shown in FIG. 12 B. There were several features across the spectra that showed differences between the cell types. The cell types could be separated easily when the pixels in the FTIR image were colour coded to the integrals of the 1591, 1334, 1215 and 1275 $cm^{-1}$ bands. For example, FIGS. 12 C and D show the 1591 and 1334 $cm^{-1}$ band integrals, respectively. To separate the cell types into two distinct groups, a HCA of the 1614-1465 $cm^{-1}$ region was performed, and the two predominant groups from a dendrogram (FIG. 13) were selected, and the pixels colour coded to distinguish the EP (red) and green for the LP (FIG. 12 E). Although spectral differences between the cell types were seen across the whole spectrum, the 1614-1465 $cm^{-1}$ region was selected because spectral differences in this region appeared to be attributed predominantly to changes in the cell type rather than changes in the disease stage.

Disease Type Differences

The disease stages in the EP and LP were analysed separately to eliminate misinterpreting spectral differences arising from cell type as differences in disease stages.

To increase the SNR, the image was first binned in 4×4 matrices, where each pixel had an approximate size of 10.8×10.8 m. However, this was still insufficient to accurately de-convolute the small signal differences that could be used to distinguish disease stages. To increase the SNR, spectra from large areas of the image were selected and averaged.

Analysis of the Epithelium

Figure 14D:
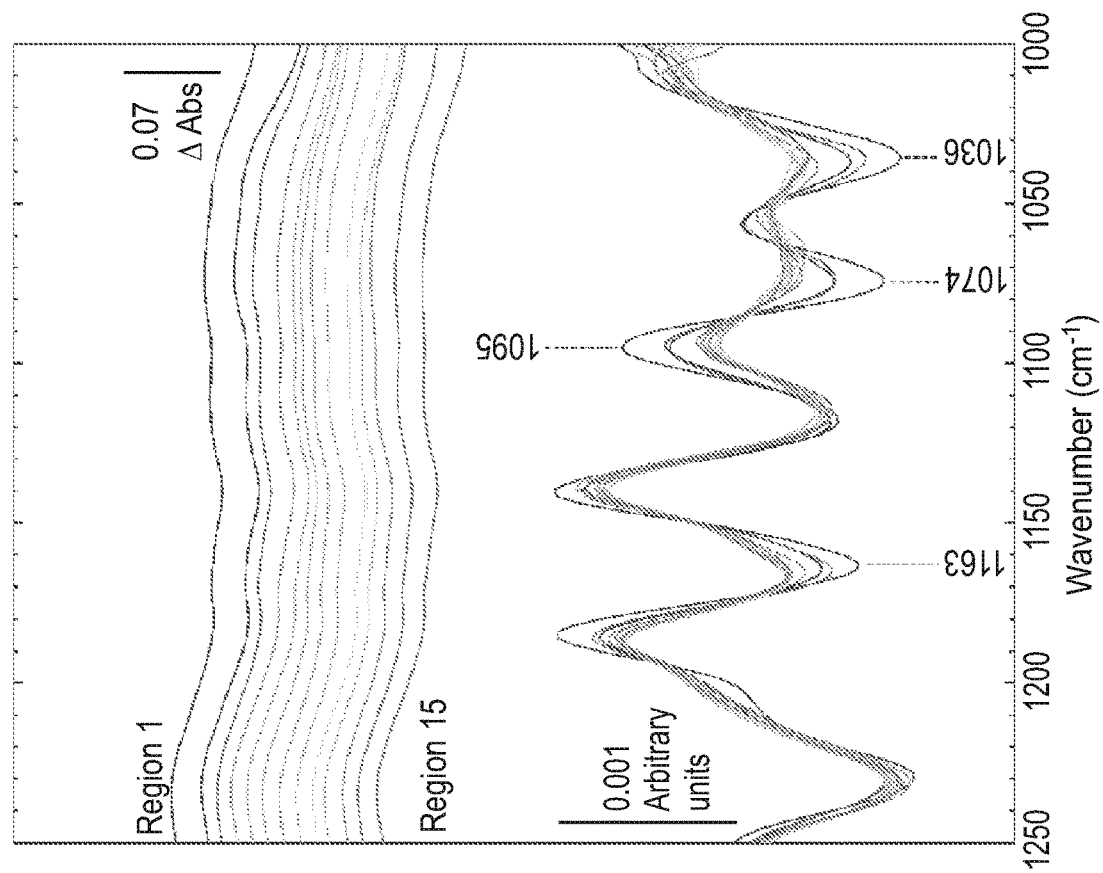
Figure 14C:
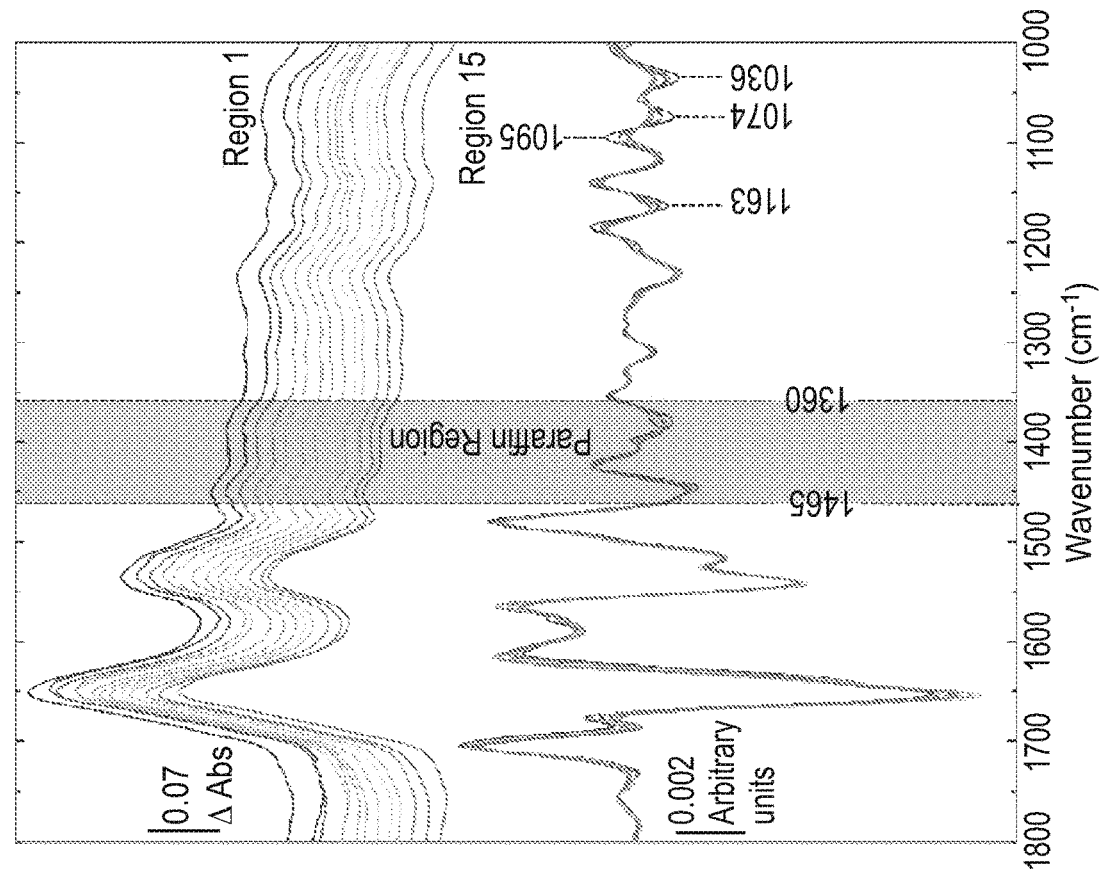

A total of fifteen areas of the image were manually selected along the EP (FIGS. 14 A and B). Areas 1-15 contain the following number of pixels, at the original resolution with a projected pixel size of 2.7×2.7 m: area 1, 2224; area 2, 992; area 3, 1392; area 4, 1344; area 5, 880; area 6, 2144; area 7, 3744; area 8, 3376; area 9, 2992; area 10, 4720; area 11, 5056; area 12, 2416; area 13, 2720; area 14, 2352 and area 15, 3280.

According to the histological analysis of the H&E stained section (FIG. 12 A), areas 1-3 were healthy, areas 4-6 exhibited mild dysplasia, areas 7-9 showed moderate dysplasia and areas 10-15 showed severe dysplasia/carcinoma in situ. The spectra within each of these areas were averaged and compared after normalisation of their amide II intensities (FIGS. 14 C and D). There were several spectral differences including the troughs at: 1163, 1074 and 1036 $cm^{-1}$ and a peak at 1093 $cm^{-1}$. These differences are clearly seen in the second derivative spectra. All aforementioned bands decreased in intensity from healthy EP (red: areas 1-3) to diseased parts of the EP (yellow/blue: areas 4-15). The p-value from a Mann-Whitney U test between healthy and dysplastic/carcinoma in situ was 0.0044 for both the 1163 and 1036 $cm^{-1}$ integrals, making the difference between healthy and dysplastic/carcinoma significant. However, there were no significant spectral differences between the mild/moderate/severe dysplasia and carcinoma in situ (areas 4-15).

Figure 15A:
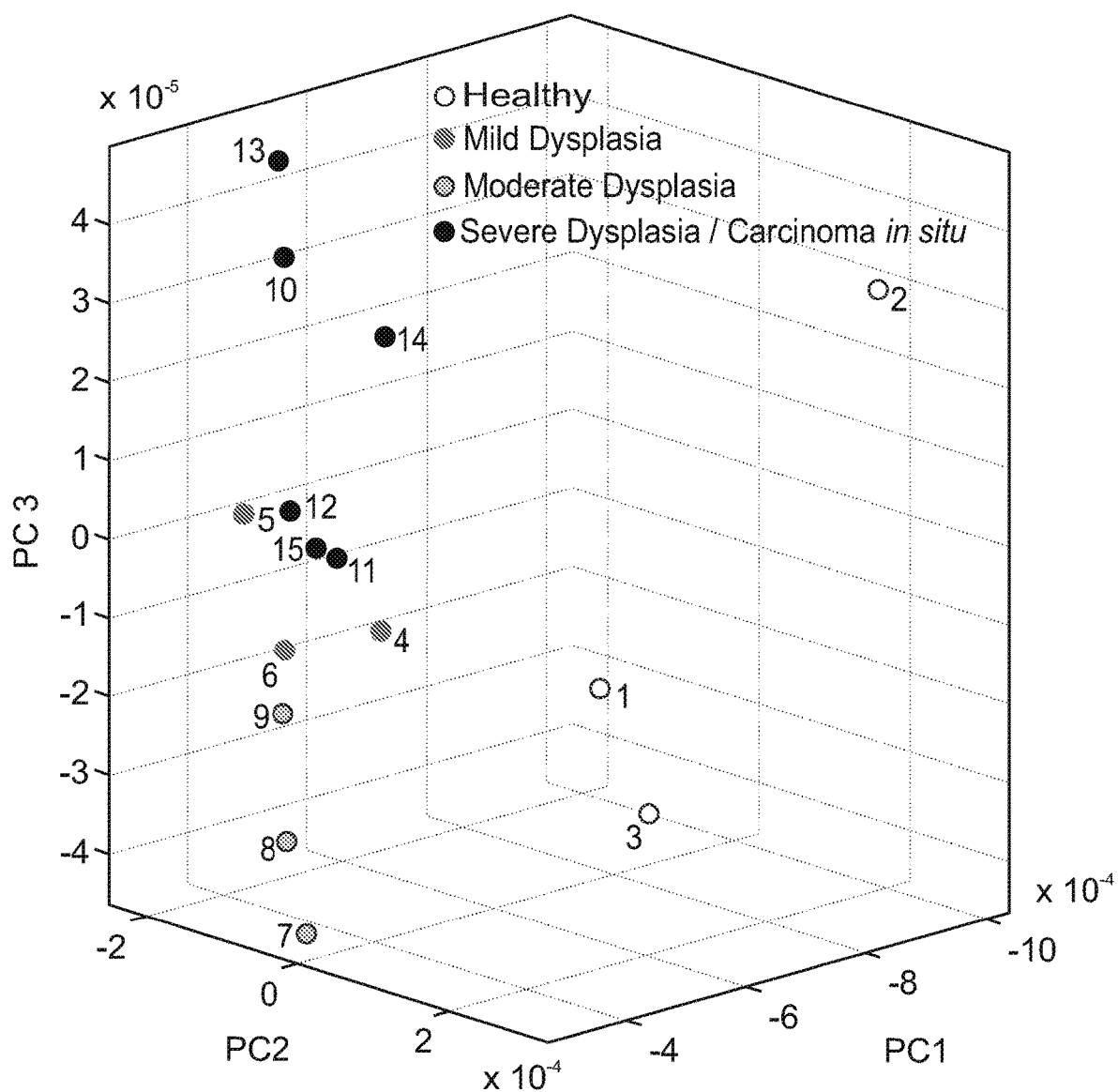
FIGS. 15A and 15B are a PCA of the spectra from the manually selected bronchial epithelium regions. A) Scatter plot showing the PCA scores from the three components of a PCA performed using the 1100-1030 $cm^{-1}$ spectral region. Each data point is labelled with its corresponding region number: green, healthy; orange, mild dysplasia; red, moderate dysplasia; black, severe dysplasia/carcinoma in situ. B) The corresponding PCA loadings.
Figure 15B:
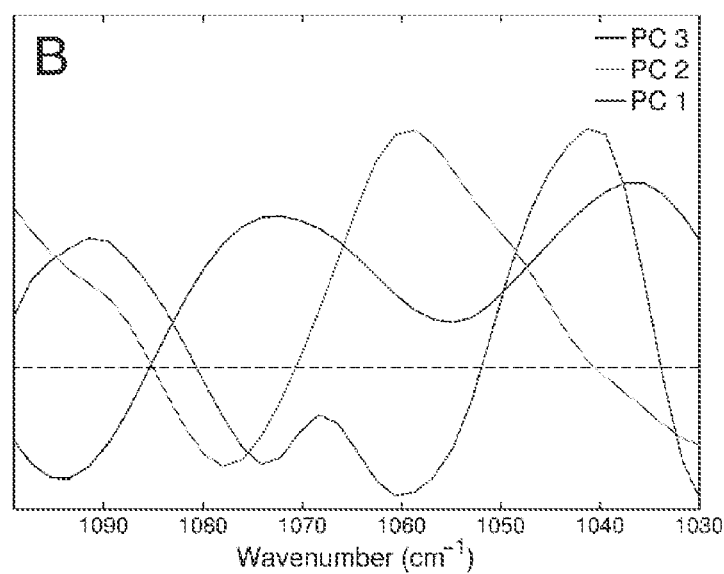
Figure 16A:
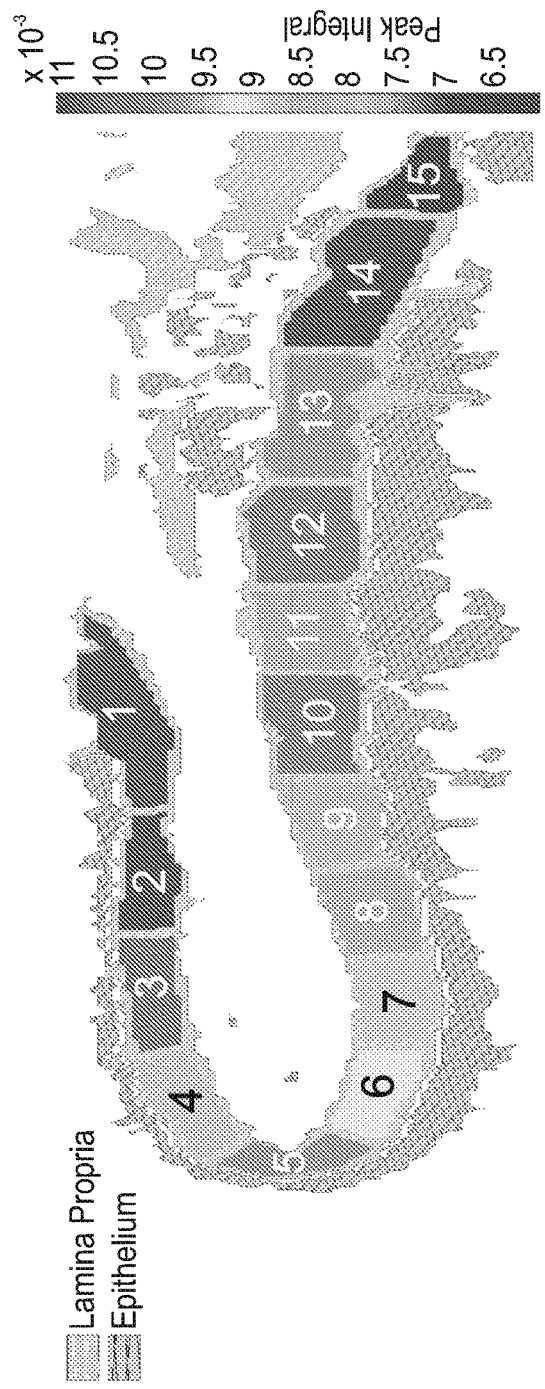
FIGS. 16A, 16 B, 16C and 16D show peak integrals of spectral features from the manually selected regions of the bronchial lamina propria. Regions of the LP colour were coded to the integrals of features at: A) 1334 $cm^{-1}$; B) 1279 $cm^{-1}$; C) 1066 $cm^{-1}$; D) 1215 $cm^{-1}$. The areas were adjacent to the following EP: areas 1-3, healthy; areas 4-6, mild dysplasia; areas 7-9, moderate dysplasia and areas 10-15, severe dysplasia/carcinoma in situ.
Figure 16B:
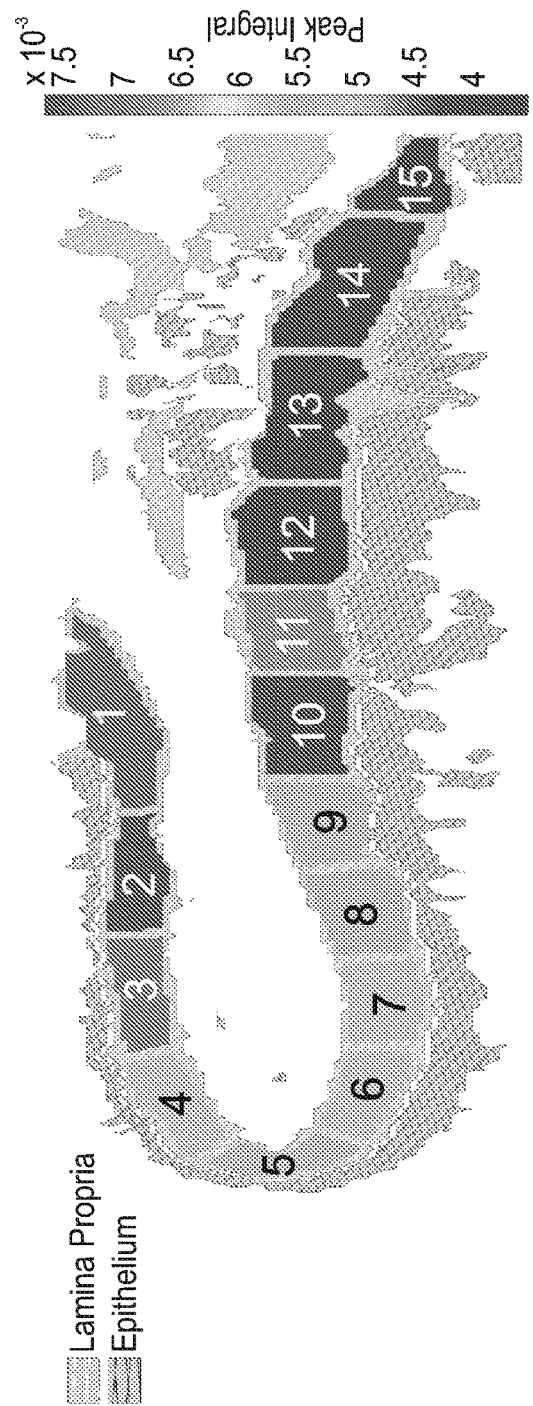
Figure 16C:
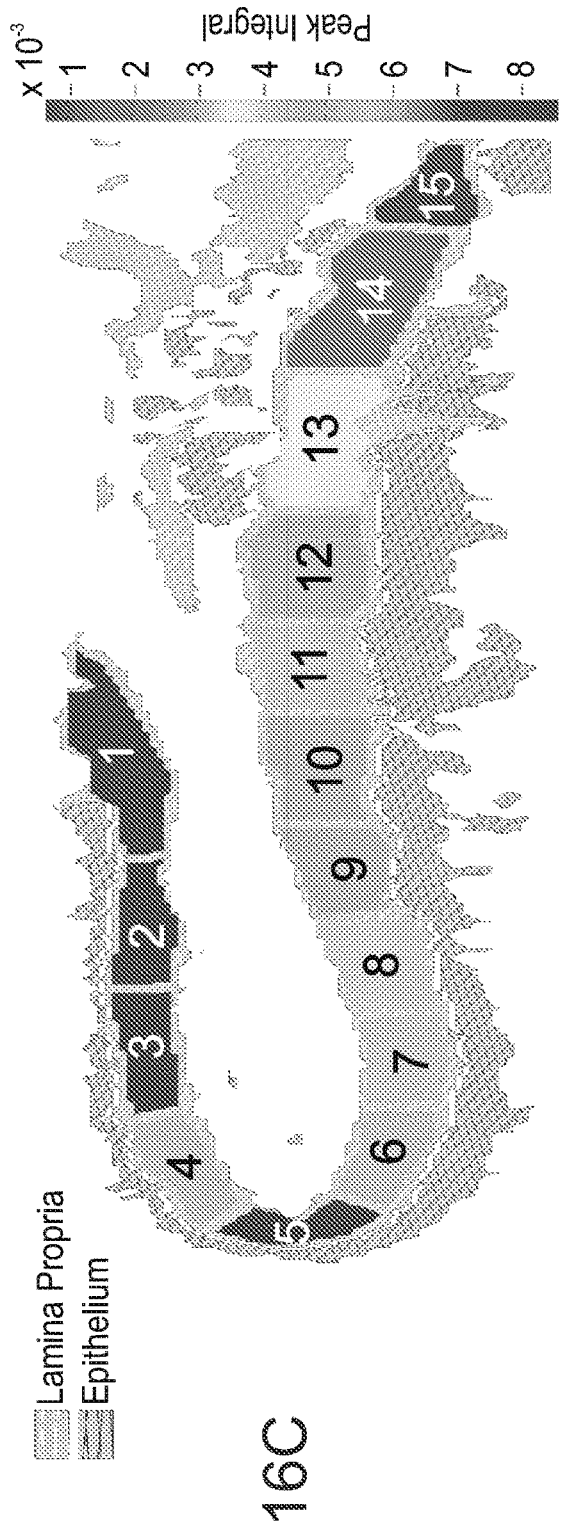
Figure 16D:
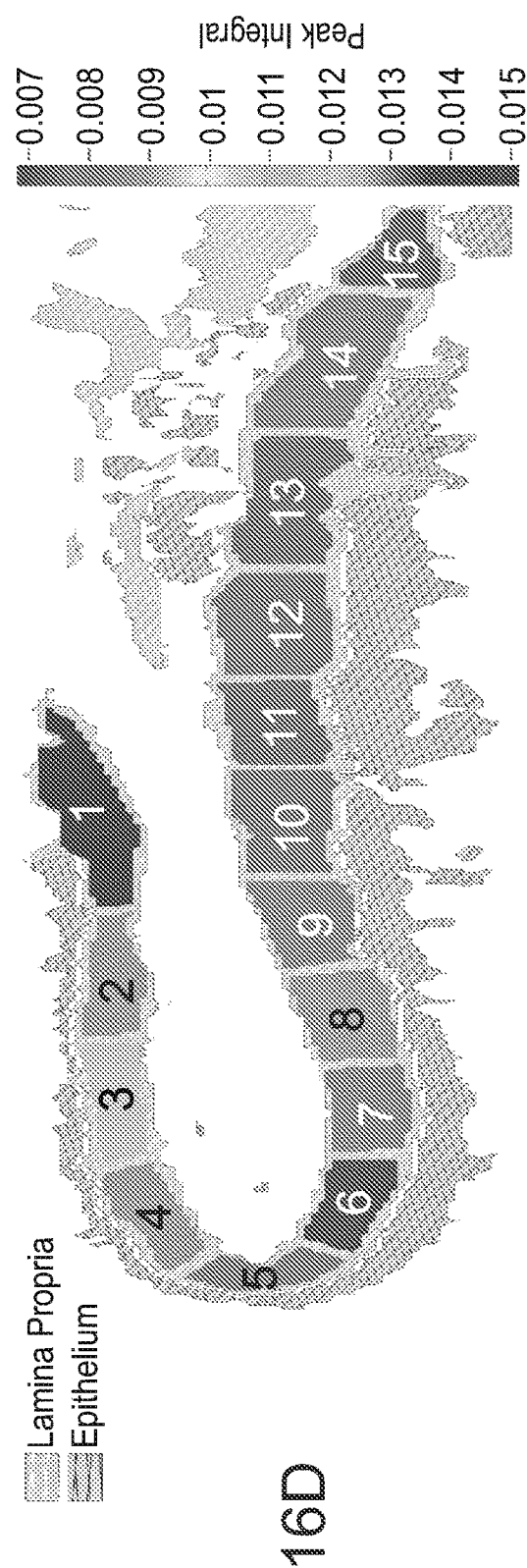

To assess whether choosing a spectral region, as opposed to a single peak, helped resolve disease stages, a three component PCA was performed on the 1100-1030 $cm^{-1}$ spectral region (FIG. 15). PC 1 separates healthy from the other dysplastic areas, and PC 3 separates moderate dysplasia from the severe dysplasia. However, there was no clear separation between the mild dysplasia and other areas of dysplasia (FIG. 15 A). It was still possible to retain good separation of disease progression by averaging spectra after subdividing each of the manually selected areas of the EP into two. However, clear separation was lost with smaller subdivisions, due to degradation of the SNR.

Analysis of the Lamina Propria

Since SCC originates in the surface EP, the major spectral differences are expected to arise in this layer of cells. To investigate whether the progression of dysplasia also affected spectral properties of the underlying tissue, fifteen LP areas were manually selected from the mapped FTIR image (FIG. 16). FIG. 17 shows the averaged absolute (top) and second derivative (bottom) spectra from these 15 areas. Areas 1-15 contain the following number of pixels at the original resolution with a projected pixel size of 2.7×2.7 m: area 1, 9360; area 2, 5232; area 3, 5264; area 4, 5008; area 5, 3376; area 6, 4896; area 7, 5536; area 8, 6544; area 9, 6288; area 10, 7872; area 11, 6576; area 12, 9072; area 13, 9296; area 14, 10704 and area 15, 4288.

The disease stage of the LP was defined according to the histopathology of the adjacent area of EP: areas 1-3, healthy; areas 4-6, mild dysplasia; areas 7-9, moderate dysplasia and areas 10-15, severe dysplasia/carcinoma in situ.

Spectral differences were evident in their second derivative troughs at 1334 and 1279 $cm^{-1}$ and peaks at 1215 and 1066 $cm^{-1}$. The intensities of these bands decreased as the disease progressed. The 1279 $cm^{-1}$ band and the 1080-1050 $cm^{-1}$ spectral region also exhibited some shifts as the disease progressed (FIG. 17 A and FIG. 17 B). FIG. 16 A-D shows the second derivative integrals of the 1334, 1279 1066 and 1215 $cm^{-1}$ bands respectively. The integrals of the 1334, 1279 and 1066 $cm^{-1}$ bands showed a gradual decrease in intensity from healthy through to severe dysplasia/carcinoma in situ. The 1215 $cm^{-1}$ integral (FIG. 16 D) also showed a decrease in intensity between healthy and dysplastic states, although there were no significant differences between the stages of dysplasia.

Figure 18A:
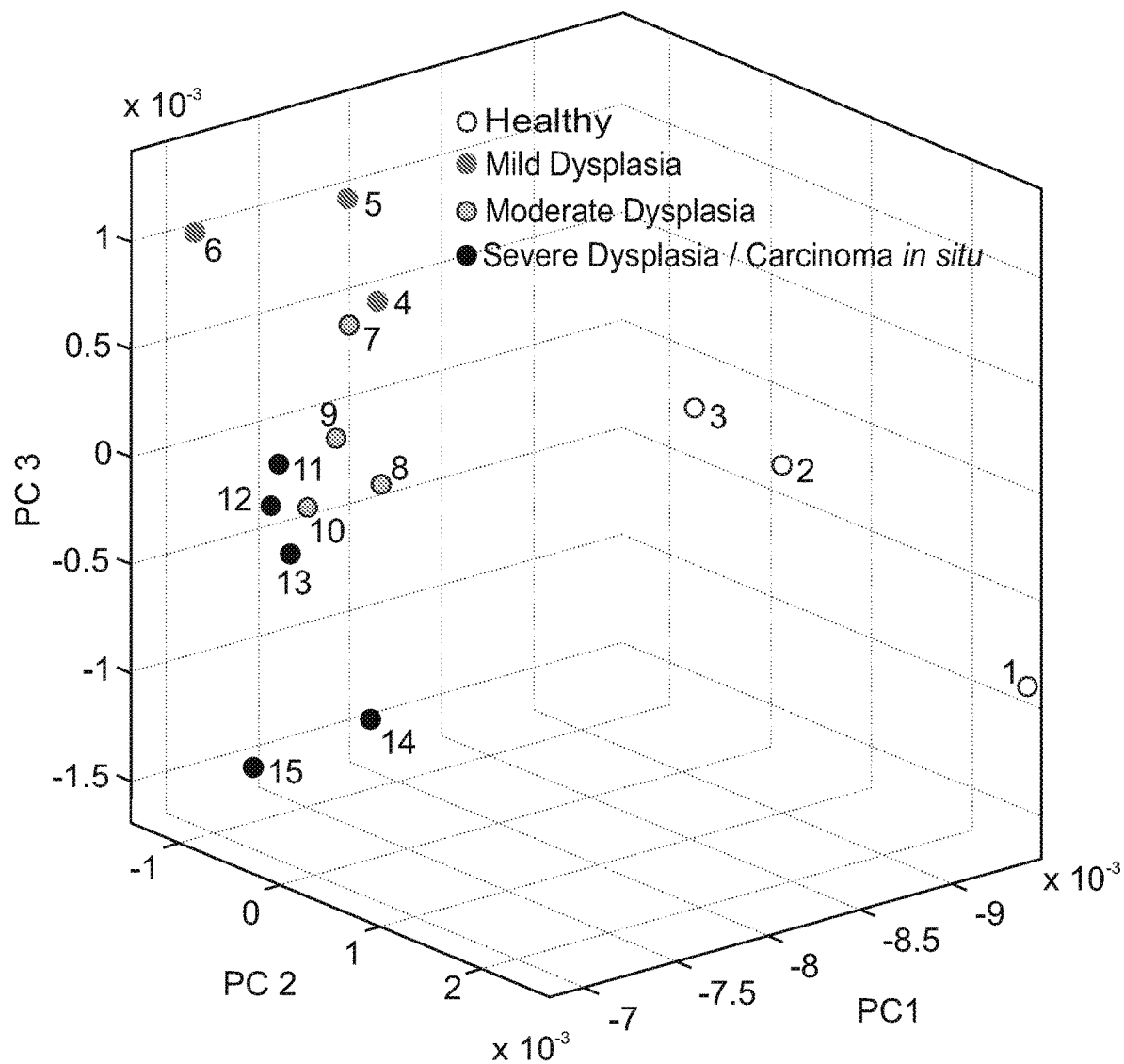
FIGS. 18A and 18B show PCA of the spectra from the bronchial lamina propria regions adjacent to the diseased epithelium. A) Scatter plot of the PCA scores from the first three components of a PCA of the 1350-1196 and 1097-1041 $cm^{-1}$ spectral regions. Each data point is labelled with its corresponding region number: green, healthy; orange, mild dysplasia; red, moderate dysplasia; black, severe dysplasia/carcinoma in situ. B) The corresponding PCA loadings.
Figure 18B:
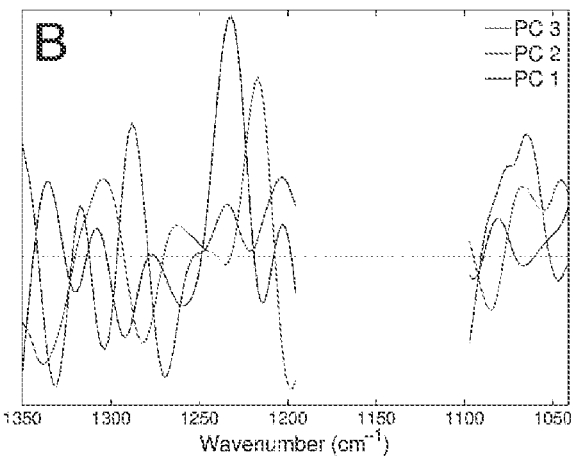

Spectral regions that contained the largest differences between disease stages in the LP are those from 1350-1196 $cm^{-1}$ and 1097-1041 $cm^{-1}$ spectral regions. FIG. 18 A shows a scatter plot of the 3 principal component scores of the 15 selected areas. The same separation between the disease stages could be seen when the areas of the FTIR image were subdivided by a factor of 4, however, this separation was lost with further subdivisions. Single peak integral analysis of the LP showed a more gradual transition from normal to carcinoma in situ that in the EP. This could be due to a higher SNR in the LP as more pixels were averaged.

Single Element ATR-FTIR Spectroscopy of Fresh Bronchial Biopsies

Assessing the Sidedness of the ATR-FTIR Bronchial Biopsies

Based on the above analysis of the 8 μm thick deparaffinised bronchial biopsy FTIR image, two cell types were expected in a typical sized biopsy (1-2 mm in diameter and up to 1 mm in thickness). Biopsies are roughly disc shaped where EP cells are expected on the surface, and LP on the underlying side.

The orientation of the biopsy on the ATR prism was not known, and, if the biopsy was twisted or folded, it was possible that the biopsy was oriented in such a way that both surface and underlying layers were in contact with the prism. Therefore, the sidedness of the biopsy could not be determined using ATR-FTIR spectroscopy alone.

To separate the spectra of fresh biopsies recorded with ATR-FTIR spectroscopy into groups based on predominant cell types (i.e. surface EP or underlying LP), the 1614-1465 $cm^{-1}$ spectral region was used in a HCA. This region of the spectrum was found to contain differences arising predominantly from cell type differences. Three main clusters were produced from the HCA, the average second derivative spectrum from these clusters can be seen in FIG. 19. Using spectral information from the ATR-FTIR spectra it was possible to assign the three spectra to different groups of cell types. One spectrum was thought to arise from EP cells (red spectrum in FIG. 19) as it had a peak at 1570 $cm^{-1}$ peak, and a more prominent amide I shoulder at 1633 $cm^{-1}$. This was consistent with findings from the FTIR imaging study (FIG. 12 B). The second main cell type was of the LP (blue spectrum in FIG. 19), this was assigned as predominantly LP due to the absence of the 1570 $cm^{-1}$ second derivative peak, and the less apparent amide I shoulder at 1633 $cm^{-1}$. The final class of spectra was predicted to be a mixture of EP and LP (green spectrum in FIG. 19), based on its similarity to the LP/EP averaged spectrum (black spectrum in FIG. 19).

Figure 19:
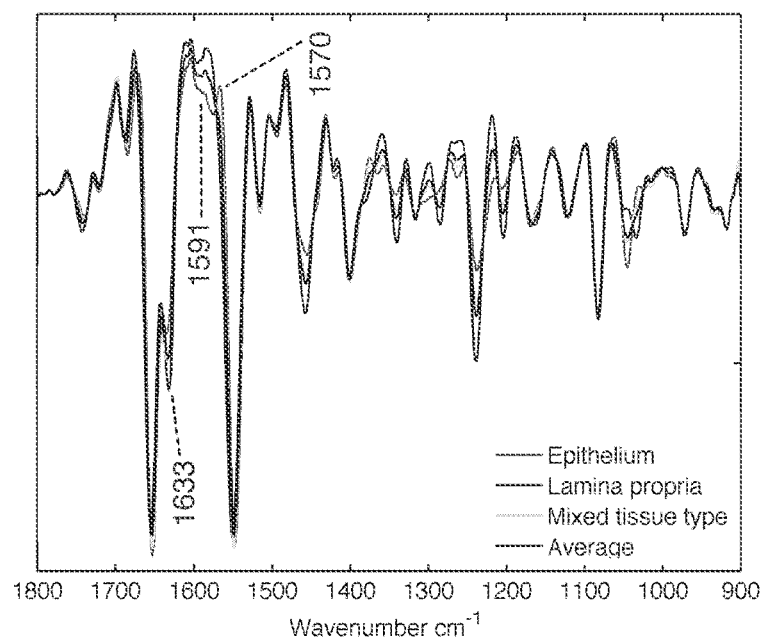
FIG. 19 shows three main clusters after HCA of the 1585-1527 $cm^{-1}$ region normalised to amide II height. The average of the EP (red) and the lamina propria (blue) signatures is shown in black, whilst the averaged IR signature of biopsies showing a mixed cell physiology is shown in green.

Table 4 shows the distribution of spectra across the three possible classes in FIG. 19. Table 4B shows whether the two spectra from a single biopsy contained spectra from either side of the biopsy. In total, 22 biopsies showed signatures containing two cell types, and only 2 of the biopsies showed spectra from the underlying LP side of the biopsy. Small forceps were used, producing biopsies with a size of 1-2 mm in diameter, the thickness of the biopsy was difficult to measure, however, it was thought to be less than 1 mm. Even with this thickness of biopsy. both the EP and LP are expected to be present. Where a biopsy either had only an EP or an LP spectrum, it was likely that biopsy was oriented in such a way that when both sides of the biopsy were measured, the same side was measured twice.

Assessing the ATR-FTIR Differences in Disease Stages of the Lung

To make accurate distinctions between disease states. The three predominant EP and LP groups were first created from the HCA (see above), before disease staging of the different groups were assessed.

Disease Stage Comparisons of Spectra From the Epithelium

Figure 20:
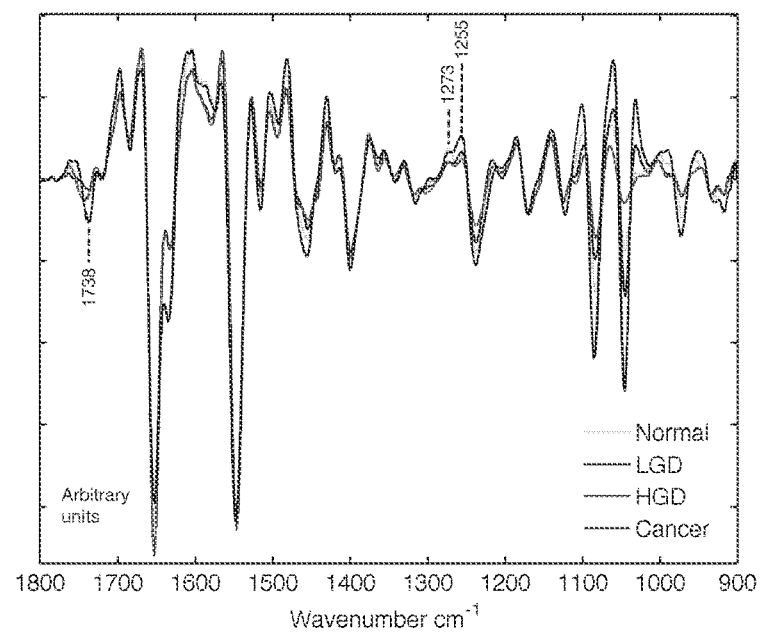
FIG. 20 shows single element ATR-FTIR comparisons of the epithelium of bronchiole biopsies. Average second derivative ATR-FTIR spectra from 41 normal EP (green) spectra (18 patients, 32 biopsies), 5 LGD EP (blue) spectra (3 patients, 4 biopsies), 8 HGD EP (red) spectra, (3 patients, 6 biopsies), and 11 cancer EP (black) spectra (3 patients, 7 biopsies). All spectra were normalised to the amide II height, with condensed water and water vapour subtracted in their absolute form.

FIG. 20 shows differences between the averaged second derivative spectra of healthy SQ, LGD, HGD and cancer disease states of the biopsies containing predominantly EP. The main differences between the disease states occurred between 1130 and 900 $cm^{-1}$, where the main contributing factors are thought to be differences in DNA/RNA and glycogen/glycoproteins, which was where most of the changes between disease stages are expected based on the previous study of the disease changes in BE tissue. The 1273 $cm^{-1}$ peak was larger in healthy tissue compared to the other diseased EP signatures, and the trough at 1738 $cm^{-1}$ in cancerous tissue was more prominent than all other stages of disease. The 1738 $cm^{-1}$ was tentatively attributed to lipid based on lipid spectra shown in 15.

Disease Stage Comparisons of Spectra From the Lamina Propria

Figure 21A:
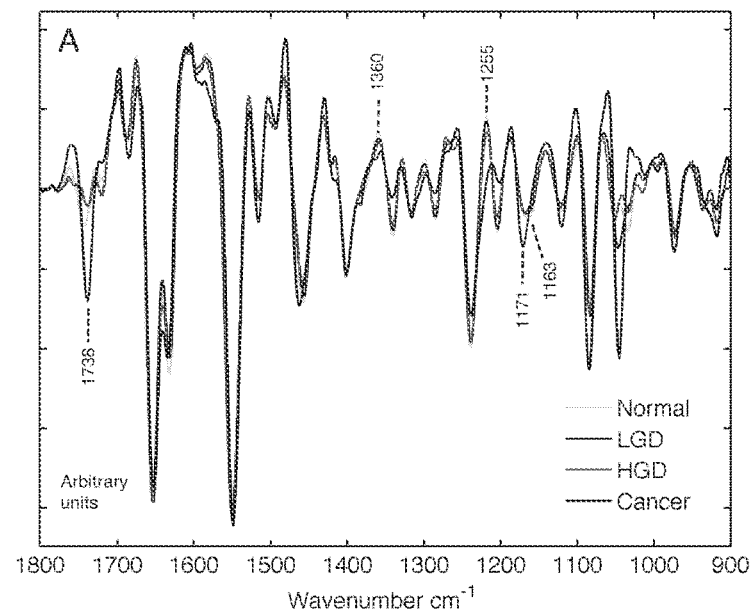
FIGS. 21A and 21B shows single element ATR-FTIR comparisons of the lamina propria of bronchiole biopsies. a) Average second derivative ATR-FTIR spectra from 16 normal LP spectra (12 patients, 14 biopsies), 2 LGD LP (blue) spectra (2 patients, 3 biopsies), 6 HGD LP (red) spectra, (4 patients, 4 biopsies), and 17 cancer LP (black) spectra (3 patients, 10 biopsies). All spectra were normalised to the amide II area in the second derivative, with condensed water and water vapour subtracted in their absolute form. b) 1190-1140 $cm^{-1}$ region showing a potential change in component composition.
Figure 21B:
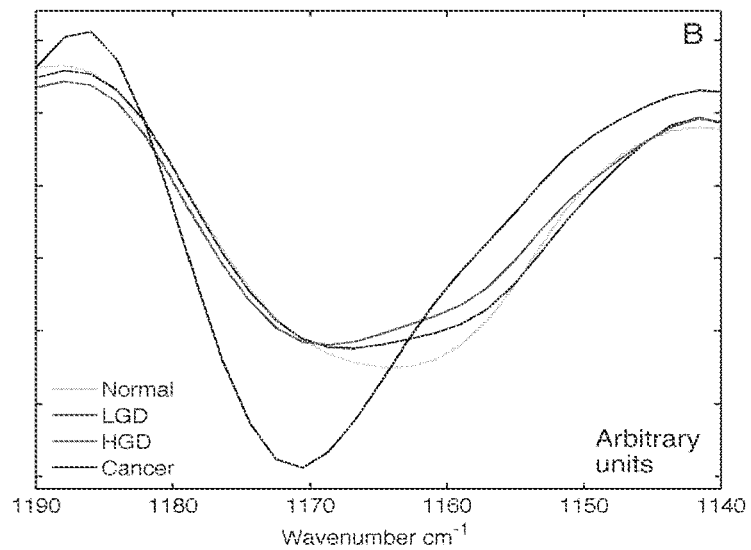

Since bronchial dysplasia develops in the EP, minimal change in the LP tissue was expected. However, the FTIR imaging study of the single biopsy suggested that the LP might also display features characteristic of the disease stage of the adjacent EP. FIG. 21 shows that there were indeed spectral differences in the LP spectra of biopsies classified as healthy SQ, LGD, HGD and cancer LP tissue, although it must be noted that the number of spectra, patients and biopsies included was small.

Normal LP shows a second derivative lipid trough at 1743 $cm^{-1}$, where as LGD, HGD and cancer have a shifted trough at 1738 $cm^{-1}$, where the trough in cancer samples was much larger than the other disease stages. There appears to be a transition from normal to cancer with a decrease in the 1360 $cm^{-1}$ second derivative peak and a total of 2 $cm^{-1}$ shift to a lower frequency. Changes in the spectral region between 1163-1171 $cm^{-1}$ were also observed. Normal LP had a single broad peak at 1163 $cm^{-1}$, where as LGD and HGD have a combination of bands at 1163 and 1171 $cm^{-1}$, and cancer has a much larger 1171 $cm^{-1}$ trough (FIG. 21 B) suggestive of an additional biochemical component appearing as the disease stage progressed.

Disease Stage Comparisons of Spectra From Mixed Cell Types

The mixed cell type group exhibited too much variation within each disease group to pick up any significant spectral differences that could be used to distinguish between them. The mixed cell type is likely present due to poor orientation of the biopsy on the prism, for example, if the biopsy was twisted, the resulting spectrum containing both the surface EP and the underlying EP. During the studies with both BE and lung cancer, one of the main drawbacks of using ATR-FTIR spectroscopy for clinical diagnosis of fresh biopsies was its orientation on the prism. The fresh lung biopsies were recorded before the sidedness issue was known. Therefore, if future collections of data were recorded, a protocol would be in place to help ensure that the biopsy was not twisted or folded. This would help prevent multiple cell types being in-contact with the prism.

Results

As with the main BE study, FTIR imaging was used to generate a library of typical cell type spectra and disease type spectra. A single 8 μm thick deparaffinised lung biopsy that contained a complete gradation of diseases from healthy to SCC in situ was used for the analysis. The cell types were significantly different and were easily separated by the integration of 1591, 1334, 1215 and 1275 $cm^{-1}$ bands, or by HCA of the 1614-1465 $cm^{-1}$ region, which was used to separate the spectra into two distinct cell type groups. There is little information present in the literature regarding spectral cell type differentiation of lung tissue. Bird et al. present an example where they used FTIR imaging to separate the different cell types in a single sample. This was done by using a 10 class HCA, which was assigned to cell/tissue types such as the LP with fibroblasts, LP with abundant lymphocytes, blood vessels, macrophages and mucinous glands. However, they did not specify the spectral features that arise from these cell types and so cannot be compared with the data here. The cell type differences found here do, however, bear similarity to the cell type differences found between the EP and LP in BE. This similarity was in the second derivative 1633 cm$^{-1}$ spectral region where there was an amide I shoulder present in the BE CEP and lung EP and absent in the BE LP and lung LP. Although, the shoulder in the lung EP was not as prominent as the BE FTIR image data. The other prominent feature that could be used to determine sidedness in the 1614-1465 cm$^{-1}$ spectral region of BE FTIR image data, was the second derivative peak at 1570 cm$^{-1}$. The differences in lung EP and LP in this region of the FTIR imaging data were not as prominent. Nevertheless, the differences in the 1570 cm$^{-1}$ bands in ATR-FTIR spectra of fresh lung EP and LP biopsies were more similar to those found between the EP and LP ATR-FTIR spectra of fresh BE biopsies. The reason that this differences was less apparent in the FTIR image data was unknown. However, it is possible that it arose because of effects of dehydration on the imaging sample spectra, which can affect the IR spectra. However, due to the consistency of spectra across the image, it is most likely that the differences in the 1614-1465 cm$^{-1}$m arose from real differences in protein types. The LP is a structural tissue comprised of a network of fibrous tissue that contains more collagen and blood vessels than the epithelium. Healthy EP is a thin layer of epithelial cells and will contain more cells than the LP. The spectral differences between the EP and LP in the 1560-1190 cm$^{-1}$ spectral region have not been assigned to any individual components due to the complex overlapping components likely to contribute to this region. However, these differences are most likely to be related to differences of the fibrous connective tissue in LP compared to the layer of EP cells which will contain more metabolites are carbohydrates.

The differences between the disease stages within the EP and LP were largely in the 1350-1000 cm$^{-1}$ spectral region. The EP demonstrated differences between healthy and dysplastic/carcinoma in situ in band integrals at 1163, 1095, 1074 and the 1036 cm$^{-1}$. However, no significant differences could be found between the intermediate dysplastic stages when comparing intensities of integrals of these components. However, some distinction between disease stages could be further resolved with a PCA of the 1100-1030 cm$^{-1}$ spectral region. However, to determine the significance of these spectral changes, more samples would be required in the study. Comparisons between the changes in the spectrum reported here and model compounds suggest that the changes in the 1074 and 1036 cm$^{-1}$ might be attributed to changes in glycogen related compounds. A recent biochemical study on a lung cancerous cell line versus a healthy cell line by Chaudhri et al. suggests that there is a decrease in metabolites, including glucose, from the healthy cells to cancerous cells, supporting this finding.

The spectral differences between the disease stages were more prominent in the LP. The main differences arose at 1334, 1279, 1215 and 1066 cm$^{-1}$ bands. The differences between the disease stages was further resolved with a PCA using the 1350-1196 and the 1097-1041 cm$^{-1}$ spectral regions. Particularly interesting was a band shape change around, 1066 cm$^{-1}$, indicative of the introduction, and/or change, of one or more biochemical components. It is known that cancer development triggers the inflammatory response. It is possible that such additional component(s) were caused by leukocytes and other cells/proteins recruited to the area in response to the inflammatory process. It was possible that changes in the 1066 cm$^{-1}$ region was due to an increase in the amount of DNA relative to protein from the additional cells from the inflammatory response. However proportional changes in other DNA bands were not seen.

Bird et al. describe the changes between SCC and healthy tissue at 1235, 1090, 1065 and 965 cm$^{-1}$, which they attributed to changes in DNA. These are in part similar to the 1095 and 1066 cm$^{-1}$ band changes seen in the present study. However, it is difficult to make direct comparisons as it was not clear whether the EP and LP had been separated in the Bird et al. study. Another FTIR imaging study of SCC and healthy lung tissue by Yano et al. reported discrimination based on the height of the 1045 cm$^{-1}$ band, when normalised to the amide II band. They attributed this change to collagen based on their previous work with pulverised fresh biopsies in FTIR transmission mode. Whilst a band at 1045 cm$^{-1}$ was not found here, a band at 1036 cm$^{-1}$ that might be related to the same component was found. However a more detailed analysis would be required to confirm this. As well as the aforementioned possible change in glycogen, DNA/RNA are well known to contributors in the 1100-900 cm$^{-1}$ spectral region. Since the EP contains more cells and therefore nuclei, it was likely that some of the changes in this 1100-900 cm$^{-1}$ region reported here were attributed to changes in DNA.

The disease stage differences between the ATR-FTIR measurements of fresh biopsies, from the predominantly EP group, was seen in the 1273 and 1738 cm$^{-1}$ bands. However, these bands only showed a difference between healthy tissue and cancerous tissue. The 1273 cm$^{-1}$ this peak was larger in healthy tissue compared to the other diseased EP signatures, however, this band was not supported by FTIR imaging. The trough at 1738 cm$^{-1}$ in cancerous tissue was more prominent than all other stages of disease. This part of the spectrum was tentatively assigned to lipid. However, this band was not observed in the FTIR imaging data, which could be due to the fact that the imaging sample was deparaffinised and this process may well have washed away lipid components. To assess whether there were any lipid changes, a more detailed analyses is required.

In conclusion, spectral differences between the EP and LP of the 8 m thick lung biopsy section could be seen in the 1614-1465 cm$^{-1}$ region of second derivative spectra; differences which were also observed between CEP and LP of BE biopsies. Spectral signatures showing disease progression in the EP of the tissue section from SQ to carcinoma in situ were seen in 1350-1000 cm$^{-1}$ region of both the EP and LP. EP features at 1163, 1095, 1074 and the 1036 cm$^{-1}$ were integrated and showed a clear distinction between SQ EP and dysplastic/carcinoma in situ tissue. However, the SNR was not high enough to distinguish between the dysplastic disease stages with integration alone. PCA of the 1100-1030 cm$^{-1}$ spectral region showed that further separation of the dysplastic stages could be achieved. Integrals of the LP features at 1334, 1279, 1215 and 1066 cm$^{-1}$ showed a clear progression from SQ to carcinoma in situ. This progression could be further resolved using PCA of the 1350-1196 and the 1097-1041 cm$^{-1}$ spectral regions.

The fresh lung biopsy dataset recorded with ATR-FTIR spectroscopy had low numbers of samples in each disease class. The biopsy spectra could be separated into their predominant cell types, which were the EP, LP and a mixed class. The differences between the cell types could be seen at the 1614-1465 cm$^{-1}$ spectral region, consistent with the cell type differences in the FTIR imaged data. The spectra that contained predominantly EP spectra showed a difference between SQ and carcinoma in the 1273 and 1738 cm$^{-1}$ bands of the second derivative spectra. However, these bands could not be used to distinguish between the LGD and HGD disease classes.

Effects of Acetic Acid

Two experiments were carried out:

1. To test the possible effects acetic acid has on tissue in a controlled environment two concentrations of acetic acid were sprayed onto porcine oesophagus. Small sections of the oesophagus were then cut and measured using IR spectroscopy.

2. The effects of acetic acid, throat spray, 1/100,000 adrenaline, NAC and throat spray on human tissue were analysed by comparing IR measurements of human biopsy tissue from patients with and without the use of the drugs.

The spectral changes associated with acetic acid on human and porcine tissue were then compared.

(i) Porcine Samples

Method

Oesophaguses from two different pigs were used, and the experiment was conducted approximately 3 hours after the pigs were slaughtered. The oesophaguses were transported from the abattoir to the lab on ice and were then dissected and washed with distilled water to remove any remaining food in the gullet.

Table 5 shows number of samples and the number of measurements recorded in each condition. All samples were handled with tweezers and between each measurement the sample was lifted and this prism cleaned with distilled water and allowed to dry.

After thoroughly washing the oesophaguses with distilled water, two samples were cut from each and measured. Part of the oesophagus was then washed with 2.5% acetic acid; the tissue was cut and immediately measured. This was repeated for the 5% acetic acid on a new area of the oesophagus.

Measurement Parameters

A Perkin Elmer Spectrum 2 fitted with a single bounce diamond ATR prism and a DTGS detector was used. Spectra were recorded in absorbance mode between 4000 and 400 $cm^{-1}$ at a 1 $cm^{-1}$ resolution with 10 co-added and averaged scans. The resolution of the spectra was then subsequently reduced to 4 $cm^{-1}$ to improve signal to noise and to equal that of the spectrometer used in the human acetic acid experiments.

Analysis

Figure 22:
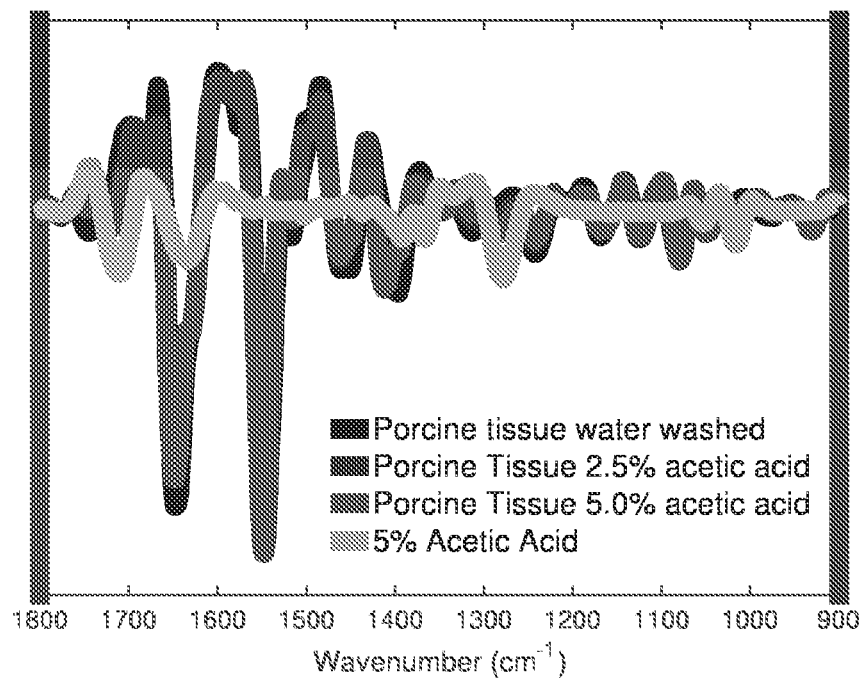
FIG. 22 shows the effect of acetic acid on porcine tissue samples. Each spectrum is the average of all spectra from the epithelium group of tissue samples: 4 spectra from tissue washed with distilled water only (black); 4 spectra from tissue washed with distilled water followed by 2.5% acetic acid (blue); 5 spectra from tissue washed with distilled water followed by 5% acetic acid (red); a single spectrum of 5% acetic acid (green).

FIG. 22 shows the effect of acetic acid on porcine tissue. There are clear and consistent band intensity changes in the tissue as the concentration of acetic acid increases which directly correspond to the 5% acetic acid reference spectrum. The bands that follow this change in intensity are at 1709, 17744, 1397, 1366, 1366, 1312, 1279, 1050 and 1013 $cm^{-1}$.

There appears to be a band in the distilled water-washed tissue at 1399 $cm^{-1}$ that was shifted to 1412 $cm^{-1}$ in the tissue samples washed with 2.5% and 5% acetic acid. This band is not consistent with the reference spectra and is most probably due to a conformational change. The main component of this band is the amide III bond in proteins, which supports a protein conformational change hypothesis.

It is possible to correct the spectra measured from tissue where acetic acid has been produced, this can be done by a simple subtraction of a spectrum of acetic acid from the sample spectrum, followed by a correctional shift of the amide III bands. Therefore the evidence presented here supports the use of our algorithm with or without the use of acetic acid.

(ii) Human Tissue

Method

During a routine endoscopy, samples were intercepted from patients consented onto the BOOST study at UCL. The samples were transported on ice and in a moist sealed environment to the lab where they were measured. Some patients did not have any topical drugs sprayed on the surface of their oesophagus during the procedure. These patients were named as 'no drugs' in this analysis. Some patients had one of the following drugs sprayed onto their oesophagus: 2.5% acetic acid, 1:100,000 adrenaline, NAC or throat spray. Table 6 shows the breakdown of patient, sample and spectra numbers.

Measurement Parameters

Spectra were recorded in absorbance mode between 4000 and 400 $cm^{-1}$ using a Bruker Optics IFS 66/s FTIR spectrometer. A liquid nitrogen cooled MCT-A detector, KBr beamsplitter and a carbon globar was used. The aperture was set to 1.5 mm and a scanner velocity of 40 kHz was used. The spectrometer was purged with dried air. All measurements were recorded at 4 $cm^{-1}$ resolution, giving a peak accuracy of approximately ±1 $cm^{-1}$. Spectra were recorded in ATR mode with a SensIR 3-reflection silicon prism with ZnSe optics, 1000 background interferograms of the clean prism surface were averaged (taken after carefully cleaning the prism with water and 100% ethanol) and, after orienting the sample onto the prism, 500 interferograms were averaged to produce a single sample absorbance spectrum. All ATR-FTIR spectra were recorded using Bruker OPUS 6.5 software.

Analysis of the Effects of Acetic Acid

Figure 23:
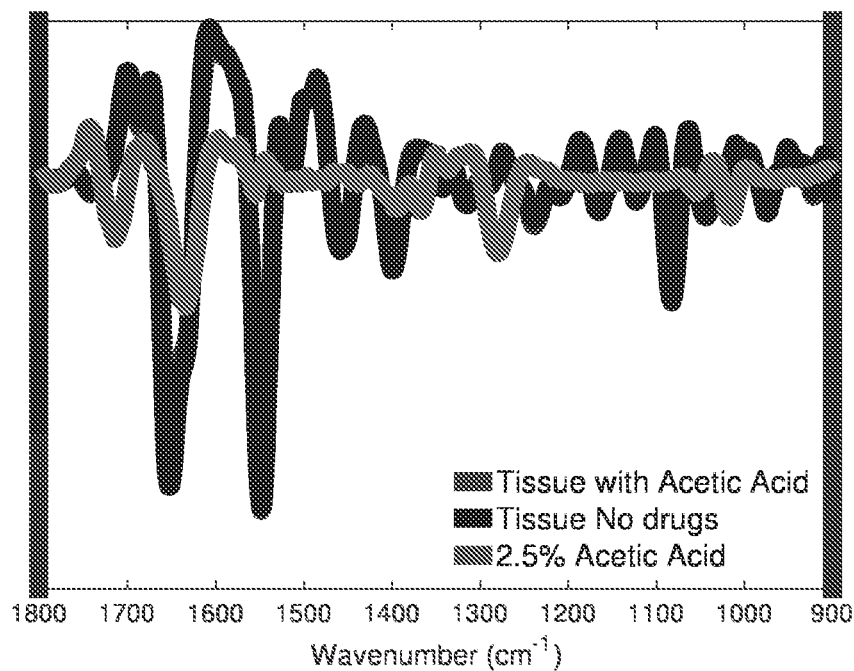
FIG. 23 shows the spectral effects of acetic acid on human tissue.

FIG. 23 shows the comparison of human tissue with and without acetic acid spray. There appears to be no evidence that the acetic acid affects the spectra. There are some small spectral differences around 1051 and 1030 $cm^{-1}$. Although, these band differences appear in a region of the spectrum where acetic acid absorbs, there are no other changes in the spectra that would support that this change is due to acetic acid. These changes are also not statistically different as they lie within the standard deviation of both groups of data.

The effects of acetic acid of porcine tissue in this experiment were much greater than the effects seen in human samples. This was to be expected as the porcine samples were prepared and analysed in a controlled environment in which the oesophagus was held horizontal, allowing the acetic acid to sit on the tissue for an extended amount of time. In reality, when acetic acid is applied in vivo to a human, it quickly runs off in to the stomach and is further washed away by saliva.

Analysis of the Effects of 1:100,000 Adrenaline

Figure 24:
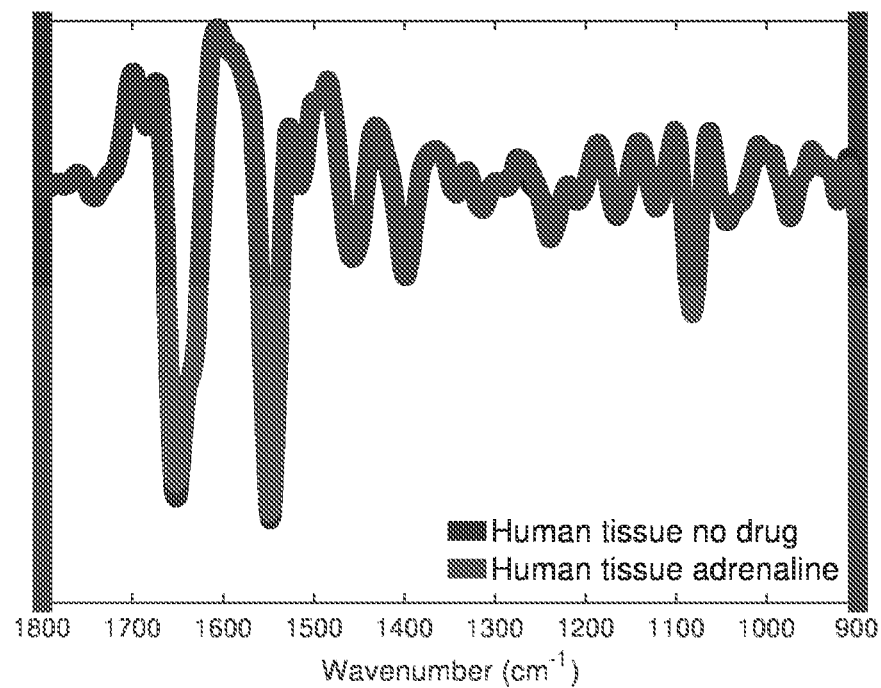
FIG. 24 shows the spectral effects of 1:100,000 adrenaline on human tissue.

The effects can be seen FIG. 24 which shows that there are only minor changes between human tissue where adrenaline had been used and human tissue where no drugs had been used. These changes are not statistically significant.

Analysis of the Effects of NAC

Figure 25:
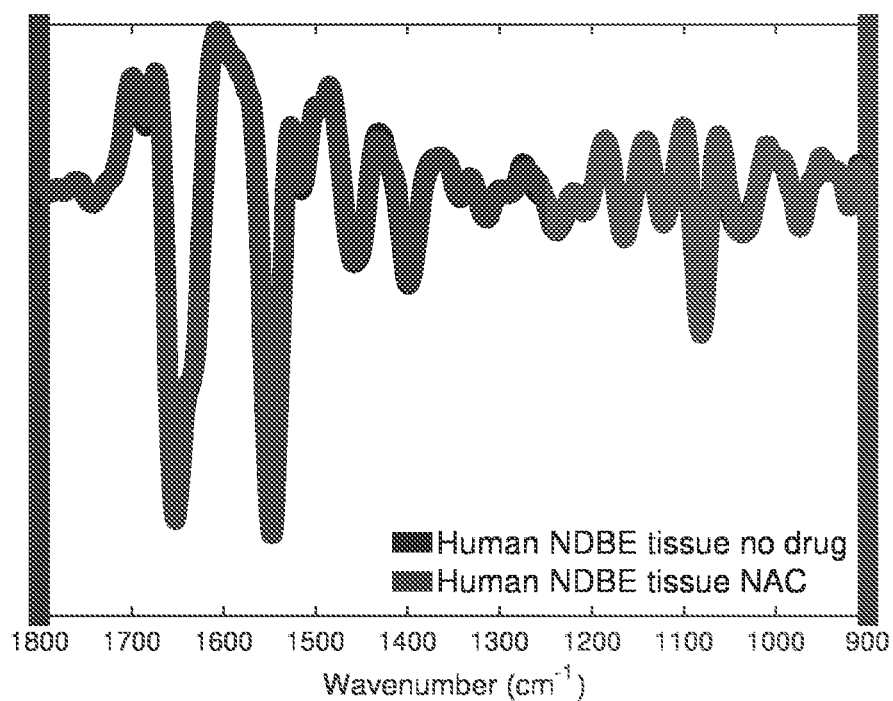
FIG. 25 shows the spectral effects of NAC on human tissue.

The effects can be seen in FIG. 25, which shows that there are only minor changes between human tissue where NAC had been used and human tissue where no drugs had been used. These changes are not statistically significant.

Analysis of the Effects of Throat Spray

Figure 26:
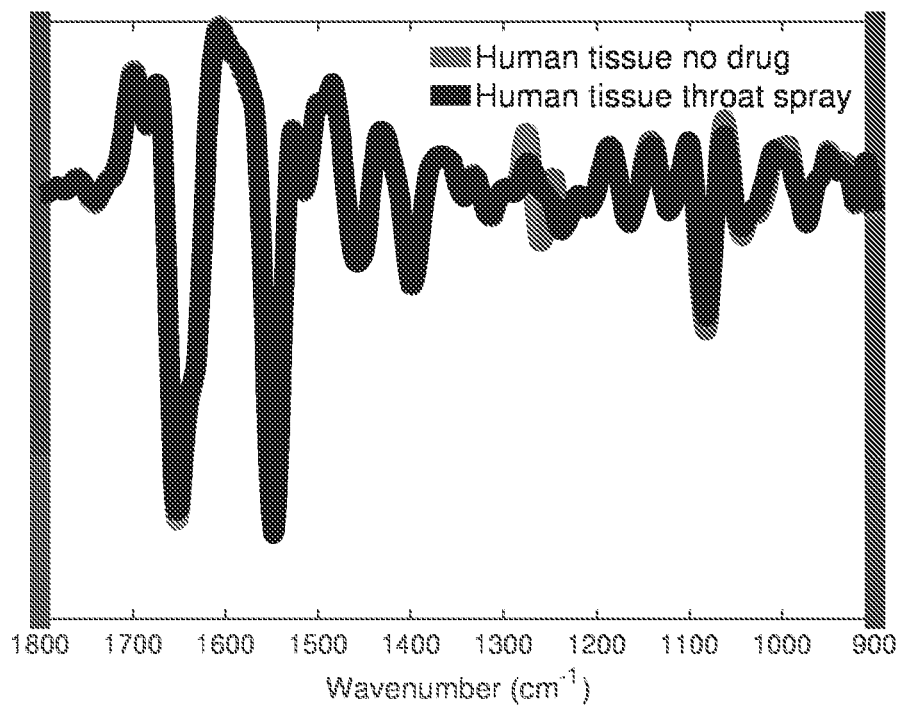
FIG. 26 shows the spectral effects of throat spray on human tissue.

The effects can be seen in FIG. 26, which shows the spectral differences between tissue with and without throat spray. The changes between 1294 and 1213 $cm^{-1}$ are statistically significant changes. However, these fall in a region of the spectrum that is not currently used in the algorithm, and therefore is not likely to influence algorithm performance. The minor spectral changes below 1110 $cm^{-1}$ are not statistically significant.

Tables

TABLE 1

Total number of patients, biopsies, and ATR-FTIR spectra recorded at each disease stage according to their histological diagnosis, after the removal of outliers.

|       | Patients | Biopsies | Spectra |
|-------|----------|----------|---------|
| SQ    | 70       | 87       | 167     |
| NDBE  | 75       | 222      | 412     |
| HGD   | 10       | 31       | 58      |
| EAC   | 21       | 39       | 73      |
| TOTAL | 122      | 379      | 710     |

TABLE 2

Confusion matrix for the prediction of SQ spectra versus NDBE/HGD/EAC spectra PLSDA with a leave-one-patient out cross validation applied to the 1385-1235 and 1192-1130 $cm^{-1}$ regions.

|                 |              | Actual class | | | |
|-----------------|--------------|----|-----------|------|------|
|                 |              | SQ | NDBE/HGD/EAC | Sen | Spe |
| Predicted class | SQ           | 107 | 7         | 0.64 | 0.99 |
|                 | NDBE/HGD/EAC | 60  | 536       | 0.99 | 0.64 |

TABLE 3

Confusion matrix for the prediction of SQ/NDBE or HGD/EAC when including an inconclusive group on a per biopsy basis.

|                 |              | Actual class | | | |
|-----------------|--------------|---------|---------|------|------|
|                 |              | SQ/NDBE | HGD/EAC | Sen  | Spe  |
| Predicted class | SQ/NDBE      | 223     | 2       | 0.83 | 0.97 |
|                 | HGD/EAC      | 46      | 60      | 0.97 | 0.83 |
|                 | Inconclusive | 60      | 7       | Inconclusive Rate: 0.18 | |

TABLE 4

Distribution of the sidedness of normal bronchiole biopsies. A) Distribution of all the spectra across the possible IR cell types B) Distribution of pairs of spectra from the same biopsy: whether they had the same cell type, different cell types, or whether the biopsy had only one spectrum.

| Table A       | Spectra |
|---------------|---------|
| Epithelium    | 41      |
| Lamina propria| 16      |
| Mixed         | 24      |
| TOTAL         | 81      |

| Table B                      | Biopsies |
|------------------------------|----------|
| Epithelium only              | 9        |
| Epithelium and lamina propria| 6        |
| Epithelium and mixed         | 14       |
| Lamina propria only          | 2        |
| Mixed only                   | 2        |
| Biopsies with single spectra | 9        |
| TOTAL                        | 42       |

TABLE 5

Pig data recorded (number of samples and the number of measurements recorded in each condition).

| Condition: Washed with | Number of Pigs | Number of samples | Number of Spectra |
|---|---|---|---|
| Distilled water only | 2 | 4 | 7 (4 from the epithelium and 3 from the underlying tissue) |
| Distilled water followed by 2.5% acetic acid | 2 | 4 | 8 (4 from the epithelium and 4 from the underlying tissue) |
| Distilled water followed by 5% acetic acid | 2 | 4 | 11 (5 from the epithelium and 6 from the underlying tissue) |

TABLE 6

Human tissue data (shows the breakdown of patient, sample and spectra numbers).

| Drug | Number of patients | Number of biopsy samples | Number of biopsy spectra |
|---|---|---|---|
| No drugs | 117 | 367 | 698 |
| 2.5% Acetic acid | 3 | 10 | 24 |
| 1:100,000 adrenaline | 4 | 8 | 16 |
| NAC | 2 | 5 | 10 |
| Throat spray | 7 | 13 | 25 |

REFERENCES

1. Bhat, S. et al. Risk of malignant progression in Barrett's esophagus patients: results from a large population-based study. *J. Natl. Cancer Inst.* 103, 1049-1057 (2011).
2. Simard, E. P., Ward, E. M., Siegel, R. & Jemal, A. Cancers with increasing incidence trends in the United States: 1999 through 2008. *CA Cancer J Clin* 62, 118-128 (2012).
3. Reid, B. J., Li, X., Galipeau, P. C. & Vaughan, T. L. Barrett's oesophagus and oesophageal adenocarcinoma: time for a new synthesis. *Nat Rev Cancer* 10, 87-101 (2010).
4. Fitzgerald, R. C. et al. British Society of Gastroenterology guidelines on the diagnosis and management of Barrett's oesophagus. *gut* 63, 7-42 (2014).
5. Haidry, R. J. et al. Radiofrequency ablation for early oesophageal squamous neoplasia: outcomes form United Kingdom registry. *World J Gastroenterol* 19, 6011-6019 (2013).
6. Haidry, R. J. et al. Improvement over time in outcomes for patients undergoing endoscopic therapy for Barrett's oesophagus-related neoplasia: 6-year experience from the first 500 patients treated in the UK patient registry. *gut* (2014). doi:10.1136/gutjnl-2014-308501
7. Levine, D. S. et al. An endoscopic biopsy protocol can differentiate high-grade dysplasia from early adenocarcinoma in Barrett's esophagus. *Gastroenterology* 105, 40-50 (1993).
8. Kerkhof, M. et al. Grading of dysplasia in Barrett's oesophagus: substantial interobserver variation between general and gastrointestinal pathologists. *Histopathology* 50, 920-927 (2007).
9. Downs-Kelly, E. et al. Poor Interobserver Agreement in the Distinction of High-Grade Dysplasia and Adenocarcinoma in Pretreatment Barrett's Esophagus Biopsies. *Am J Gastroenterol* 103, 2333-2340 (2008).
10. Chisholm, J. A., Mayne, G. C., Hussey, D. J. & Watson, D. I. Molecular biomarkers and ablative therapies for Barrett's esophagus. *Expert Review of Gastroenterology & Hepatology* 6, 567-581 (2012).
11. Sharma, P. et al. Standard endoscopy with random biopsies versus narrow band imaging targeted biopsies in Barrett's oesophagus: a prospective, international, randomised controlled trial. *gut* 62, 15-21 (2012).
12. Curvers, W. et al. Mucosal morphology in Barrett's esophagus: interobserver agreement and role of narrow band imaging. *Endoscopy* 40, 799-805 (2008).
13. Curvers, W. L. et al. Endoscopic trimodal imaging versus standard video endoscopy for detection of early Barrett's neoplasia: a multicenter, randomized, crossover study in general practice. *Gastrointestinal Endoscopy* 73, 195-203 (2011).
14. Evans, J. A. & Nishioka, N. S. The Use of Optical Coherence Tomography in Screening and Surveillance of Barrett's Esophagus. *Clinical Gastroenterology and Hepatology* 3, S8-S11 (2005).
15. Lovat, L. & Bown, S. Elastic scattering spectroscopy for detection of dysplasia in Barrett's esophagus. *Gastrointestinal Endoscopy Clinics of North America* 14, 507-517 (2004).
16. Zhu, Y. et al. Elastic scattering spectroscopy for detection of cancer risk in Barrett's esophagus: experimental and clinical validation of error removal by orthogonal subtraction for increasing accuracy. *J Biomed Opt* 14, 044022-044022-7 (2009).
17. Sturm, M. B. et al. In Vivo Molecular Imaging of Barrett's Esophagus With Confocal Laser Endomicroscopy. *Gastroenterology* 145, 56-58 (2013).
18. Goetz, M. & Kiesslich, R. Confocal endomicroscopy: In vivo diagnosis of neoplastic lesions of the gastrointestinal tract. *Anticancer Res* 28, 353-360 (2008).
19. Estores, D. & Velanovich, V. Barrett esophagus: epidemiology, pathogenesis, diagnosis, and management. *Current Problems in Surgery* 50, 192-226 (2013).
20. Almond, L. M. & Barr, H. Advanced endoscopic imaging in Barrett's oesophagus. *International Journal of Surgery* 10, 236-241 (2012).
21. Diem, M. et al. Applications of Infrared and Raman Microspectroscopy of Cells and Tissue in Medical Diagnostics: Present Status and Future Promises. *Spectroscopy: An International Journal* 27, 463-496 (2012).
22. Kendall, C. et al. Vibrational spectroscopy: a clinical tool for cancer diagnostics. *Analyst* 134, 1029-1045 (2009).
23. Wang, T. D. et al. Detection of endogenous biomolecules in Barrett's esophagus by Fourier transform infrared spectroscopy. *Proc Natl Acad Sci USA* 104, 15864-15869 (2007).
24. Quaroni, L. & Casson, A. G. Characterization of Barrett esophagus and esophageal adenocarcinoma by Fourier-transform infrared microscopy. *Analyst* 134, 1240-1246 (2009).
25. Zhao, R., Quaroni, L. & Casson, A. G. Fourier transform infrared (FTIR) spectromicroscopic characterization of stem-like cell populations in human esophageal normal and adenocarcinoma cell lines. *Analyst* 135, 53-61 (2009).
26. Maziak, D. E. et al. Fourier-transform infrared spectroscopic study of characteristic molecular structure in cancer cells of esophagus: an exploratory study. *Cancer Detect. Prev.* 31, 244-253 (2007).
27. Wang, J.-S. et al. FT-IR spectroscopic analysis of normal and cancerous tissues of esophagus. *World J Gastroenterol* 9, 1897-1899 (2003).
28. Kendall, C. A. et al. Raman spectroscopy for the diagnosis of dysplasia in columnar and squamous epithelium. in 4161, 131-137 (*SPIE*, 2000).
29. Shetty, G., Kendall, C., Shepherd, N., Stone, N. & Barr, H. Raman spectroscopy: elucidation of biochemical changes in carcinogenesis of oesophagus. *Br. J. Cancer* 94, 1460-1464 (2006).
30. Li, S.-X. et al. Study of support vector machine and serum surface-enhanced Raman spectroscopy for noninvasive esophageal cancer detection. *J Biomed Opt* 18, 027008-027008 (2013).
31. Kendall, C. et al. Raman spectroscopy, a potential tool for the objective identification and classification of neoplasia in Barrett's oesophagus. *J. Pathol.* 200, 602-609 (2003).
32. Hutchings, J., Kendall, C., Shepherd, N., Barr, H. & Stone, N. Evaluation of linear discriminant analysis for automated Raman histological mapping of esophageal high-grade dysplasia. *J Biomed Opt* 15, 066015-066015 (2010).
33. Almond, L. M. et al. Endoscopic Raman spectroscopy enables objective diagnosis of dysplasia in Barrett's esophagus. *Gastrointestinal Endoscopy* 79, 37-45 (2014).
34. Kazarian, S. G. & Chan, K. L. A. ATR-FTIR spectroscopic imaging: recent advances and applications to biological systems. *Analyst* 138, 1940 (2013).
35. Almond, L. M. et al. Assessment of a custom-built Raman spectroscopic probe for diagnosis of early oesophageal neoplasia. *J Biomed Opt* 17, 81421-81421 (2012).

36. Kendall, C. et al. Evaluation of Raman probe for oesophageal cancer diagnostics. *Analyst* 135, 3038-3041 (2010).
37. Gajjar, K. et al. Diagnostic segregation of human brain tumours using Fourier-transform infrared and/or Raman spectroscopy coupled with discriminant analysis. *Anal. Methods* 5, 89 (2012).
38. Dorling, K. M. & Baker, M. J. Rapid FTIR chemical imaging: highlighting FPA detectors. *Trends Biotechnol.* 31, 437-438 (2013).
39. De Jong, S. SIMPLS: an alternative approach to partial least squares regression. *Chemometrics and Intelligent Laboratory Systems* 18, 251-263 (1993).

What is claimed is:

1. A method for analysing a sample obtained from a subject, comprising the steps of:
   a. providing a spectrum produced by spectrally scanning the sample using a single crystal element ATR infrared spectroscopy technique, wherein the spectrum is an average spectrum over a substantial part of the sample; and
   b. identifying one or more tissue types in the sample according to the spectrum each such tissue type produces; wherein the identifying comprises a combination of steps of:
      (i) assigning the spectrum to either: a first classification; or a squamous classification, wherein the first classification includes but does not distinguish between non-dysplastic, high-grade-dysplastic and cancerous tissue types;
      (ii) assigning a spectrum from the first classification to either: an epithelial classification; or a lamina propria classification;
      (iii a) assigning an epithelial spectrum to either: a non-dysplastic classification; or a high-grade-dysplastic or cancerous classification;
      (iii b) assigning a lamina propria spectrum to either: a non-dysplastic classification; or a high-grade-dysplastic or cancerous classification; and
   c. determining the presence or absence of a disease state depending on whether high-grade-dysplastic or cancerous tissue types are identified in the sample.

2. A method according to claim 1, wherein the identifying further comprises combining classification results from two spectra, one from each side of the sample.

3. A method according to claim 1, wherein the sample is epithelial tissue from the esophagus.

4. A method according to claim 3, wherein the sample comprises two or more constituent tissue types, including a predominant tissue type and at least one minority tissue type.

5. A method according to claim 1, wherein the method includes the step of obtaining the sample.

6. A method according to claim 1, wherein the method includes the step of obtaining the spectrum.

7. A method according to claim 1, wherein assigning the spectrum under step (i) to either: the first classification; or the squamous classification is on the basis of 1385-1235 and 1192-1130 $cm^{-1}$ spectral regions and/or the spectral region around 1153 $cm^{-1}$.

8. A method according to claim 1, wherein assigning a spectrum from the first classification under step (ii) to either: the epithelial classification; or the lamina propria classification is on the basis of the spectral region around 1570 $cm^{-1}$ and/or a 1610-1465 $cm^{-1}$ spectral region.

9. A method according to claim 1, wherein assigning an epithelial spectrum under step (iii a) to either: the non-dysplastic classification; or the high-grade-dysplastic or cancerous classification is on the basis of a 1200-900 $cm^{-1}$ spectral region, preferably a 1100-900 $cm^{-1}$ spectral region, further preferably the spectral regions around 1082, 1043, and 974 $cm^{-1}$.

10. A method according to claim 1, wherein assigning a lamina propria spectrum under step (iii b) to either: the non-dysplastic classification; or the high-grade-dysplastic or cancerous classification is on the basis of 1290-1210 and 1130-870 $cm^{-1}$ spectral regions, preferably the spectral regions around 1221 and 1047 $cm^{-1}$.

11. A method according to claim 1, wherein the method also comprises the step of shifting or calibrating the spectrum to take into account the hydration of the sample.

12. A computer programme comprising code means to carry out the method of claim 1.

13. A computer readable medium carrying a computer programme according to claim 12.

14. A system comprising a computer enabled to run the computer programme according to claim 12.

15. A system according to claim 14, further comprising a spectrometer.

16. A system according to claim 14, further comprising a library of spectra from known cells.

17. A method for diagnosing a disease state in a subject, comprising analysing a sample from the subject using the method of claim 1, wherein the presence of non-healthy cells or cells having a particular disease state is indicative of the subject having the disease state.

18. A method according to claim 1, wherein step b) is performed by comparing the spectrum to a reference data set.

19. A method according to claim 18 wherein the reference data set are spectra of samples with a known specified disease and/or disease state produced using a spectroscopy technique with microscopic resolution.

* * * * *